(12) United States Patent
Hayashi et al.

(10) Patent No.: US 9,957,392 B2
(45) Date of Patent: May 1, 2018

(54) FLUORESCENT PROBE FOR IMAGING LYMPH NODES

(71) Applicant: Eisai R&D Management Co., Ltd., Bunkyo-ku, Tokyo (JP)

(72) Inventors: Hideki Hayashi, Chiba (JP); Masanori Fujinami, Chiba (JP); Taro Toyota, Chiba (JP); Yutaka Tamura, Chiba (JP); Akira Aoki, Kyoto (JP); Yutaka Muraki, Kyoto (JP); Kazuki Onoue, Kyoto (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 8 days.

(21) Appl. No.: 15/010,612

(22) Filed: Jan. 29, 2016

(65) Prior Publication Data

US 2016/0222211 A1 Aug. 4, 2016

Related U.S. Application Data

(62) Division of application No. 13/700,780, filed as application No. PCT/JP2011/003069 on May 31, 2011, now Pat. No. 9,302,018.

(30) Foreign Application Priority Data

May 31, 2010 (JP) .................................. 2010-124252

(51) Int. Cl.
| | |
|---|---|
| *C09B 23/08* | (2006.01) |
| *A61K 49/00* | (2006.01) |
| *C07D 209/60* | (2006.01) |
| *A61K 9/127* | (2006.01) |

(52) U.S. Cl.
CPC ............ *C09B 23/083* (2013.01); *A61K 9/127* (2013.01); *A61K 49/0032* (2013.01); *A61K 49/0034* (2013.01); *A61K 49/0084* (2013.01); *C07D 209/60* (2013.01); *C09B 23/086* (2013.01)

(58) Field of Classification Search
CPC ................................. A61K 49/00; A61K 9/00
See application file for complete search history.

(56) References Cited

U.S. PATENT DOCUMENTS

| | | | |
|---|---|---|---|
| 4,968,479 A | 11/1990 | Ogiya et al. | |
| 5,571,388 A | 11/1996 | Patonay et al. | |
| 6,350,431 B1 | 2/2002 | Snow et al. | |
| 2002/0013531 A1* | 1/2002 | Hayashi ............ | A61K 49/0034 600/476 |
| 2003/0157021 A1 | 8/2003 | Klaveness et al. | |
| 2005/0069494 A1 | 3/2005 | Li et al. | |
| 2008/0056989 A1 | 3/2008 | Achilefu et al. | |
| 2009/0214436 A1* | 8/2009 | Achilefu ............ | A61K 49/0056 424/9.6 |

FOREIGN PATENT DOCUMENTS

| | | |
|---|---|---|
| CN | 1179108 | 4/1998 |
| EP | 1 149 591 | 10/2001 |
| JP | 07-191029 | 7/1995 |
| JP | 8-47400 | 2/1996 |
| JP | 10-513175 | 12/1998 |
| JP | H11217328 A | 8/1999 |
| JP | 2001-299676 | 10/2001 |
| JP | 2002-504894 | 2/2002 |
| JP | 2004-077659 | 3/2004 |
| JP | 2005-211355 | 8/2005 |
| JP | 2005220045 A | 8/2005 |
| JP | 2010-215572 | 9/2010 |
| JP | 2011184329 A | 9/2011 |
| WO | WO 96/23524 | 8/1996 |
| WO | WO1998/48838 | 11/1998 |
| WO | WO-1999/013916 | * 3/1999 |
| WO | WO 02/088666 | 11/2002 |
| WO | WO2007/091661 | 8/2007 |

OTHER PUBLICATIONS

Hui, S.W. et al., "The Role of Helper Lipids in Cationic Liposome-Mediated Gene Transfer," *Biophysical Journal*, (1996), 71:590-599.
Office Action issued in CN App. Ser. No. 201180037120.3, dated Sep. 2, 2014, 19 pages (with English translation).
Office Action issued in Japanese Application No. 2012-518252, dated Dec. 1, 2015, 2 pages.
Surace, C. et al., "Lipoplexes Targeting the CD44 Hyaluronic Acid Receptor for Efficient Transfection of Breast Cancer Cell", Molecular Pharmaceuticals, 6(4):1062-1073, 2009.
Yoneya et al., "Binding Properties of Indocyanine Green in Human Blood", *IOVS* 39(7):1286-1290, 1998.
Zhang, et al., "Near-Infrared Dichromic Fluorescent Carbocyanine Molecules", Angew. Chem. Int. Ed., 47:3584-3587, 2008.
Extended European Search Report issued in EP Application No. 11789459.2, dated May 18, 2016, 9 pages.
Zhang, Z. et al., "Near-Infrared Dichromic Fluorescent Carbocyanine Molecules", Angew. Chem. 120:3640-3643 (2008).
Decision to Grant issued in Japanese Application No. 2016-188336, dated Oct. 3, 2017, 3 pages.

* cited by examiner

*Primary Examiner* — Jake M Vu
*Assistant Examiner* — Jagadishwar R Samala
(74) *Attorney, Agent, or Firm* — Fish & Richardson P.C.

(57) ABSTRACT

Disclosed is a near-infrared fluorescent imaging agent comprising an indocyanine-based fluorescent dye and a liposome. The near-infrared fluorescent imaging agent of the present invention demonstrates high fluorescence intensity and a long anchoring time in sentinel lymph nodes, thereby making it useful for detecting sentinel lymph nodes in sentinel lymph node navigation surgery. Also disclosed is an indocyanine green derivative that is particularly suitable for use in the near-infrared fluorescent imaging agent of the present invention.

27 Claims, 9 Drawing Sheets

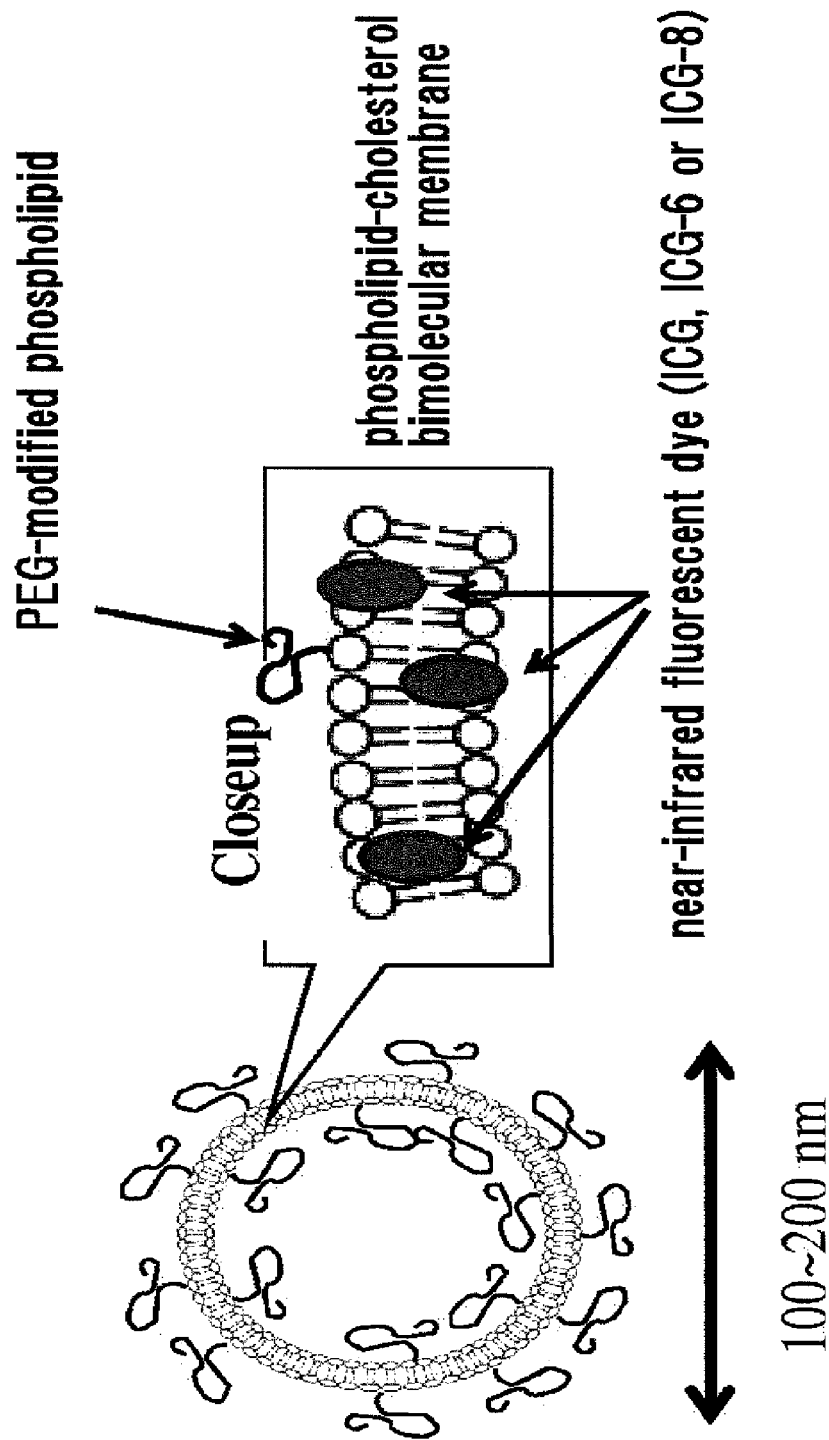
[Fig. 1]

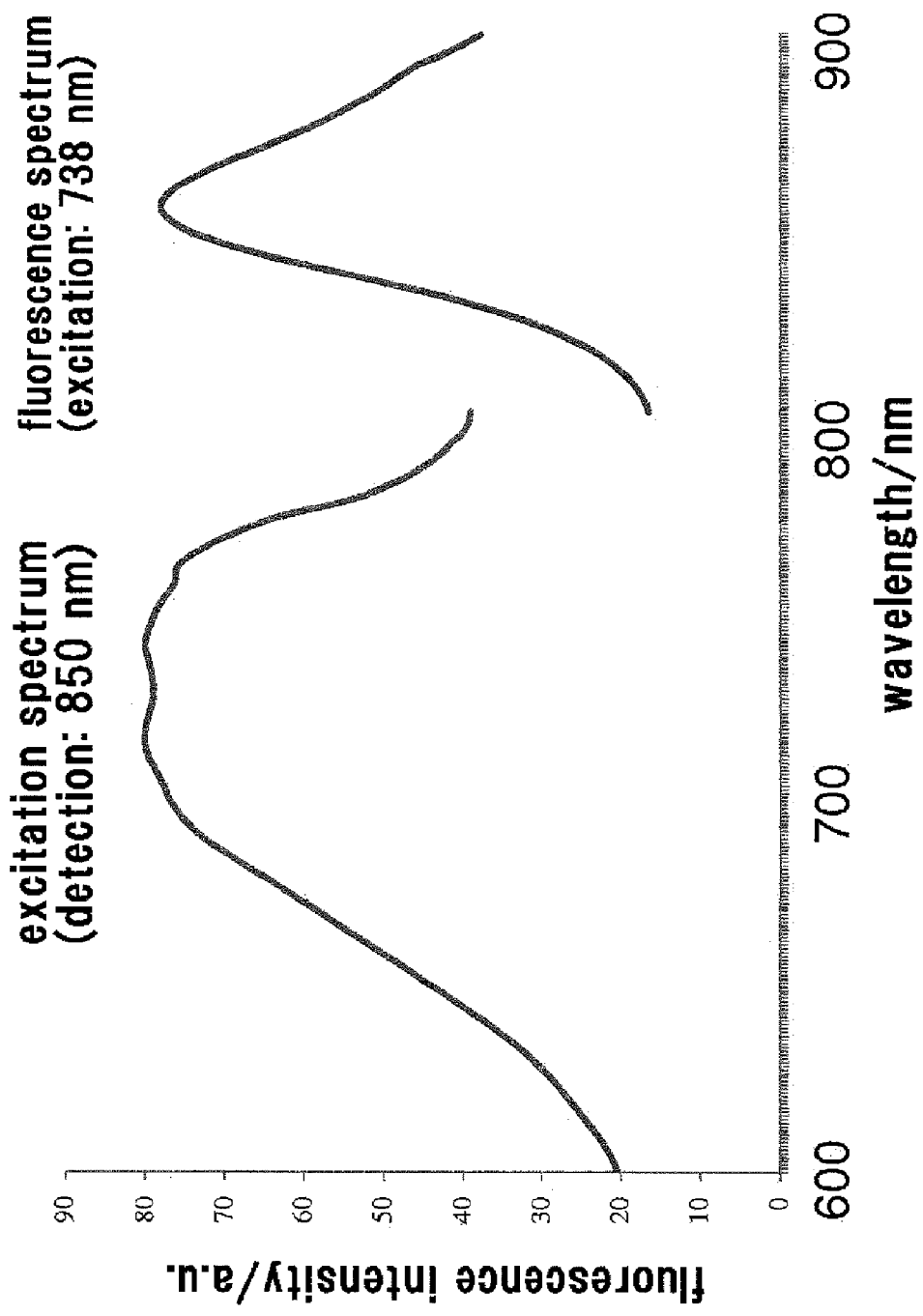
[Fig. 2]

[Fig. 3A]
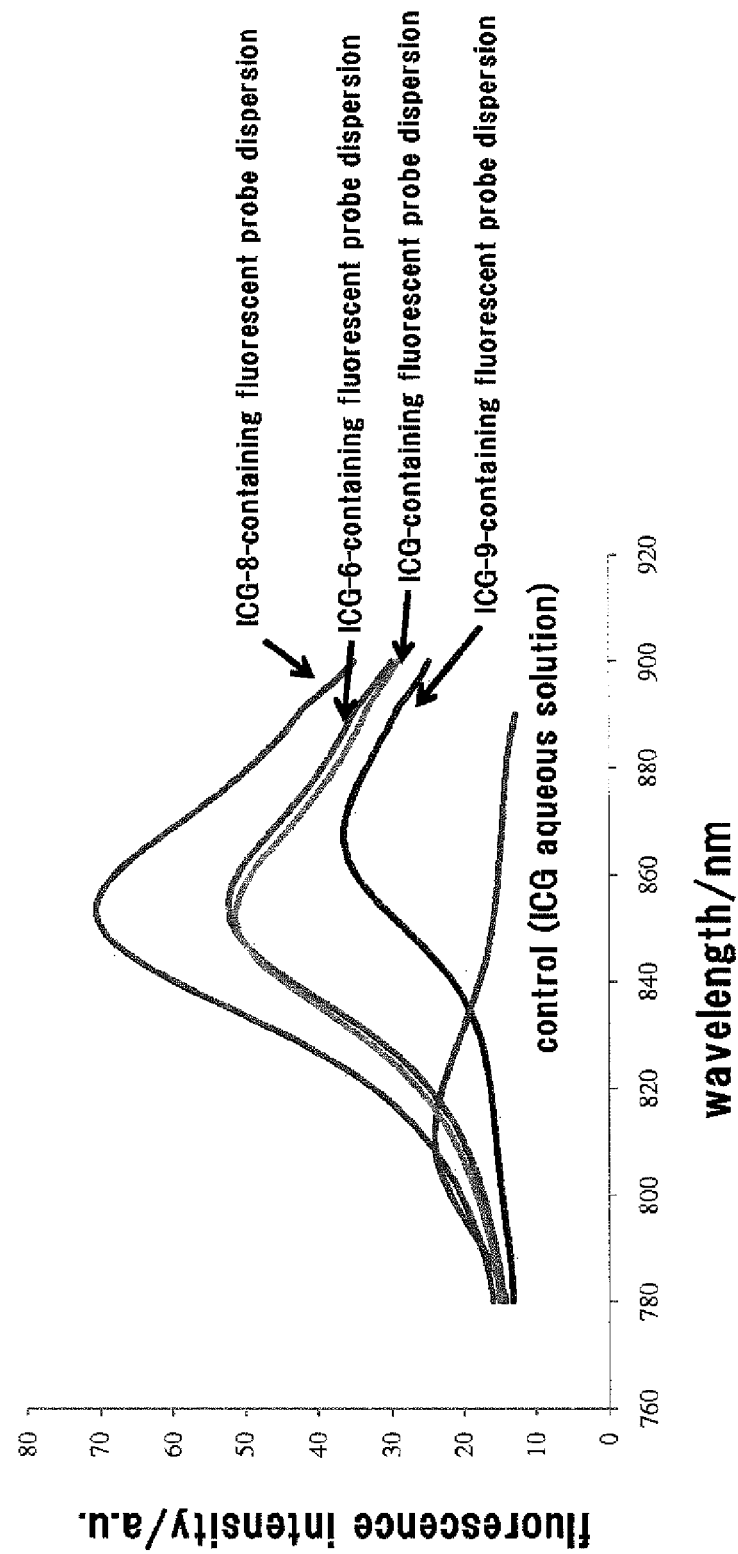

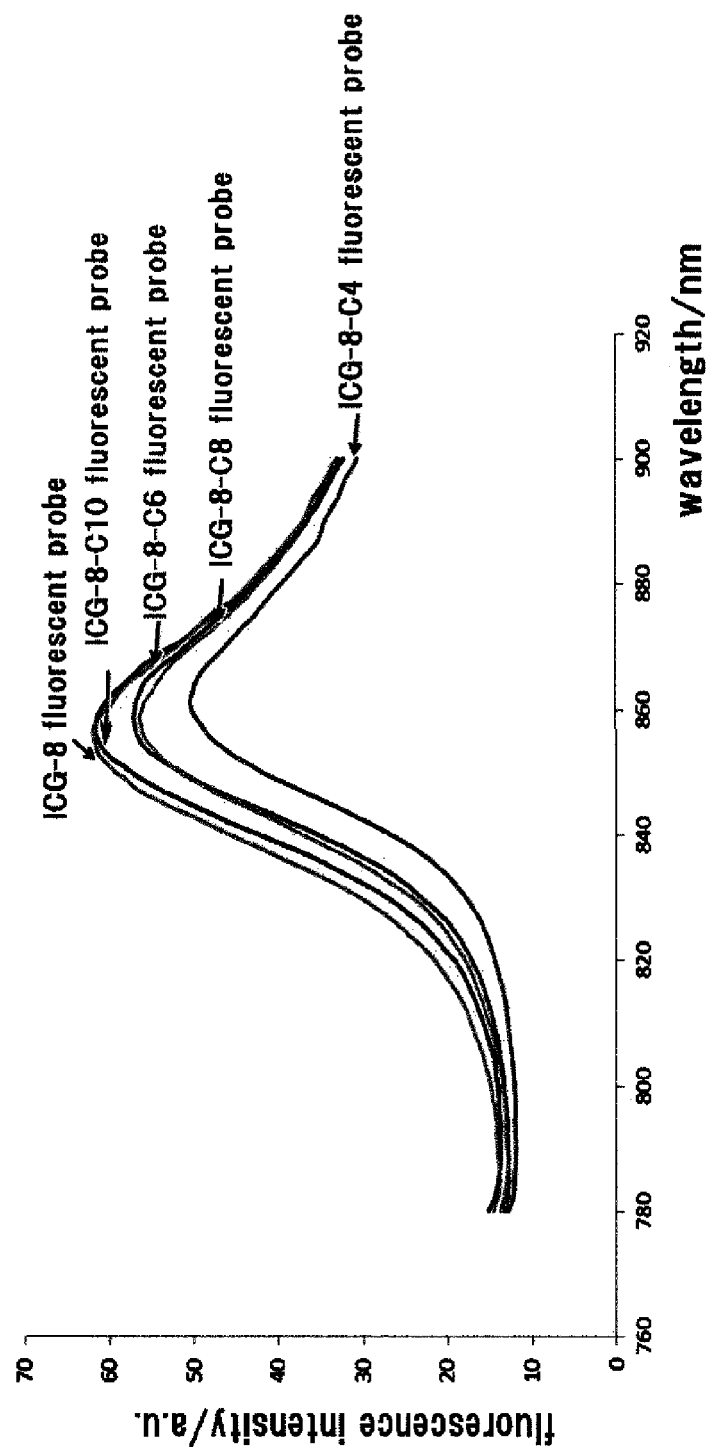
[Fig. 3B]

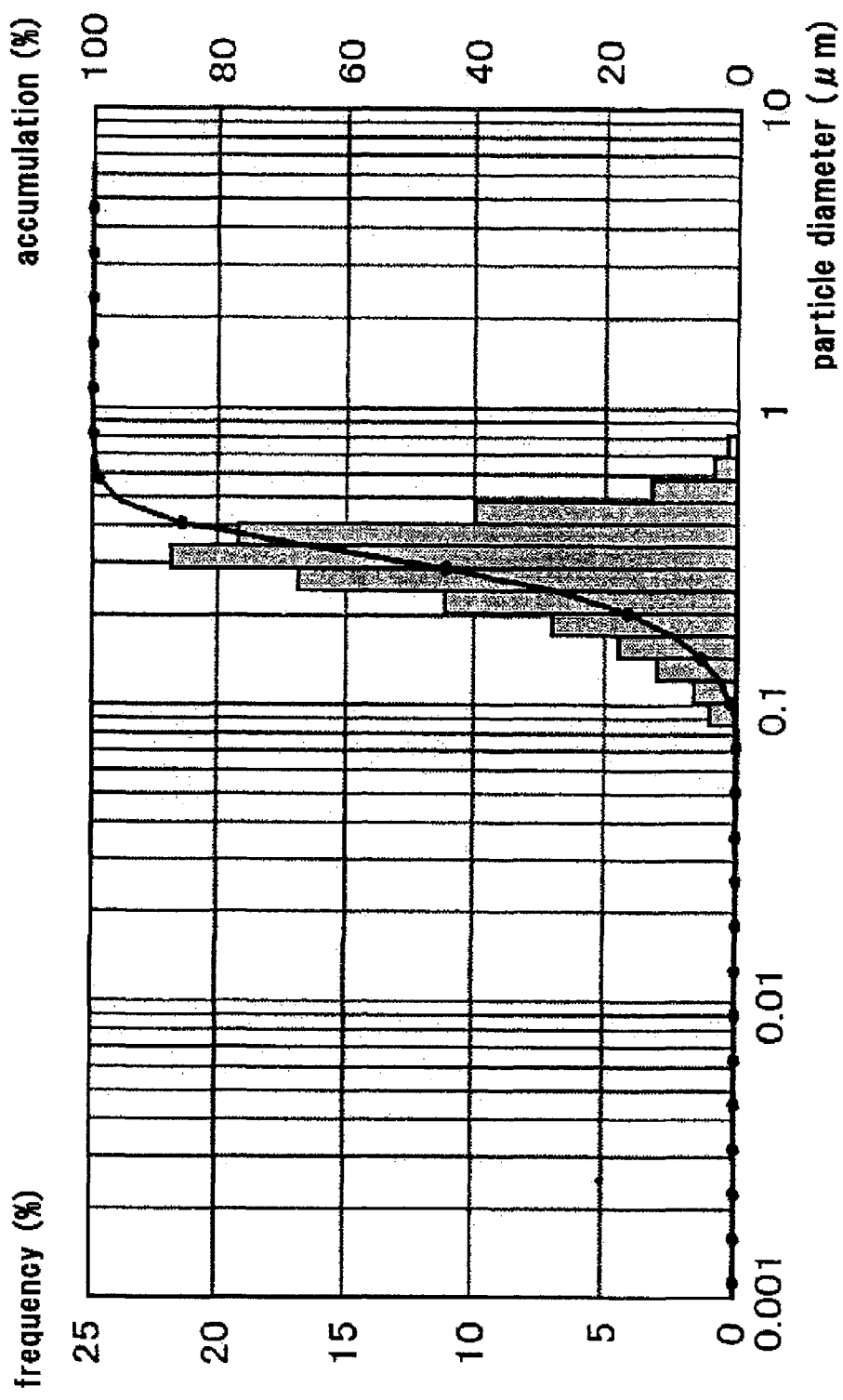
[Fig. 4]

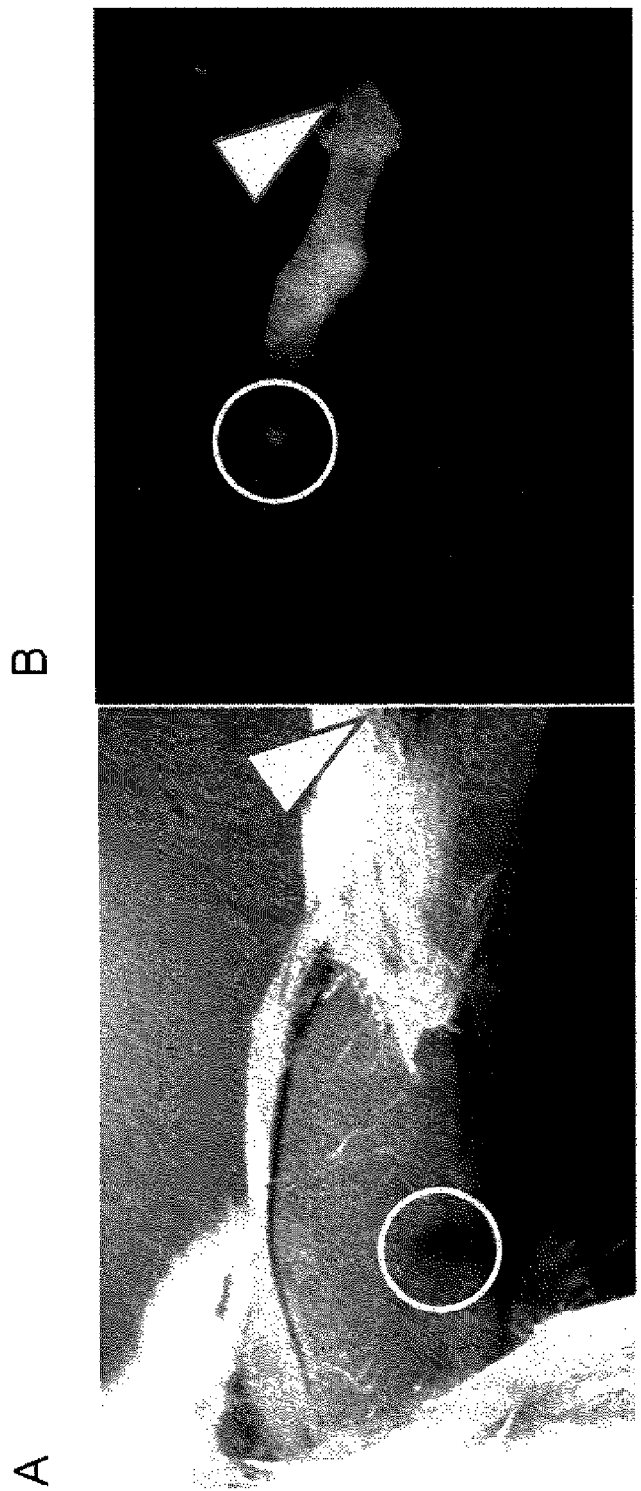
[Fig. 5]

[Fig. 6]
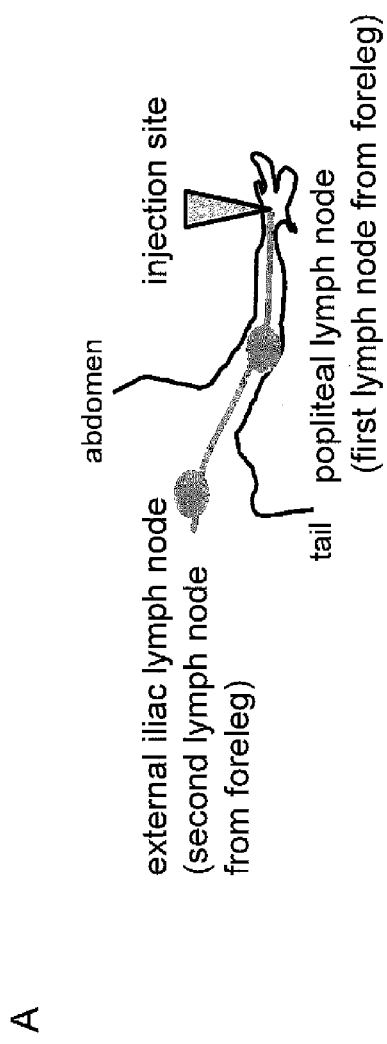
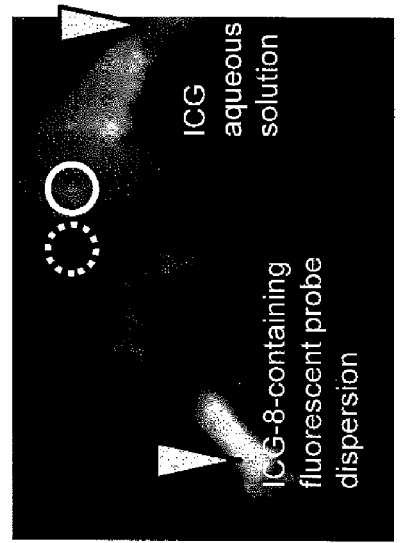
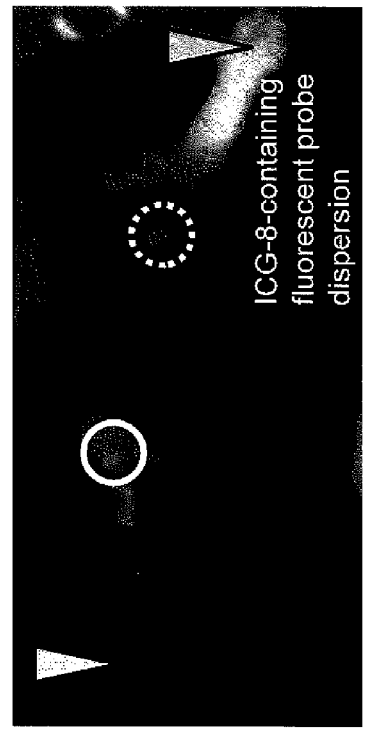

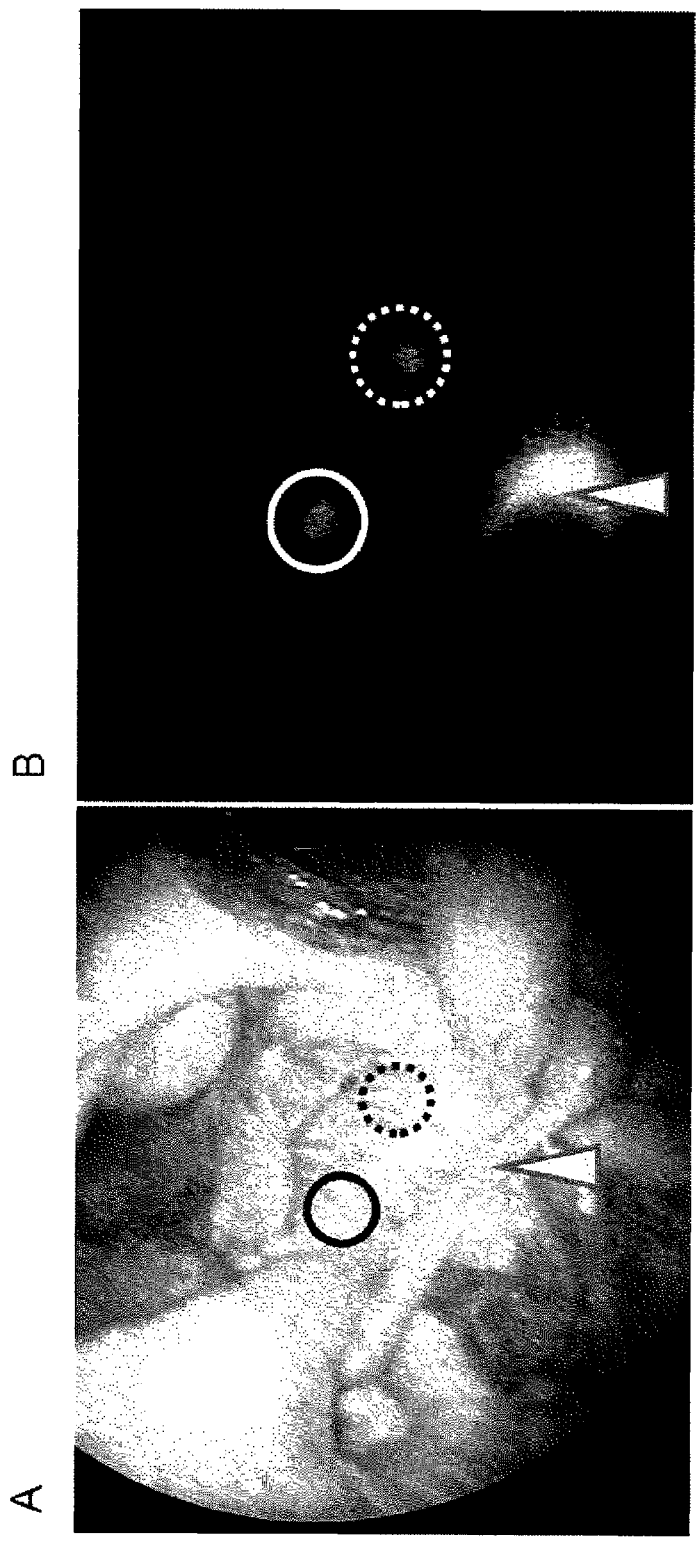

[Fig. 8]
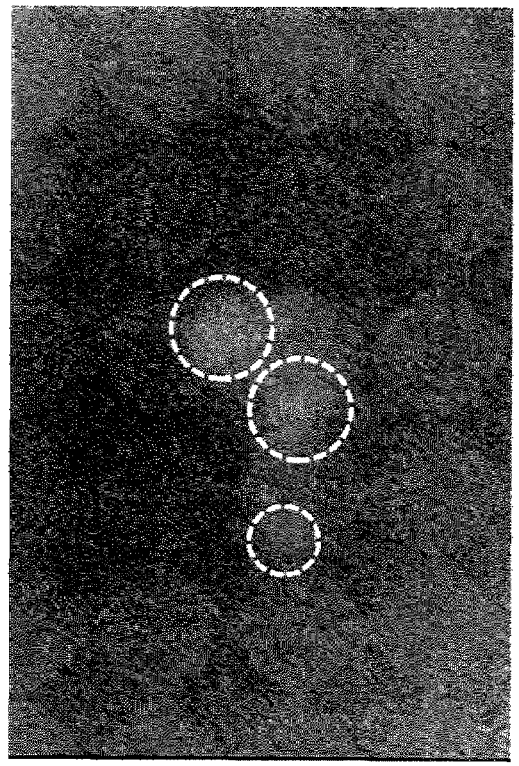

FLUORESCENT PROBE FOR IMAGING LYMPH NODES

RELATED APPLICATION

The present application claims priority on the basis of Japanese Patent Application No. 2010-124252 (filed on May 31, 2010), the contents of which are incorporated herein by reference.

TECHNICAL FIELD

The present invention relates to near-infrared fluorescent imaging of biological tissue.

BACKGROUND ART

Sentinel lymph nodes refer to lymph nodes that directly receive the flow of lymph from the primary lesion of a tumor, and are believed to be the location where lymph node metastasis first occurs. In surgical excision for early-stage cancer, a procedure known as sentinel lymph node navigation surgery is becoming increasingly common. The procedure comprises identifying the sentinel lymph node using a dye or radioactive colloid, excising the lymph node during surgery, examining for the presence or absence of metastasis, and then determining the resection range based on that result. The use of this procedure makes it possible to avoid unnecessary removal of lymph nodes in the case where evidence of metastasis is not found in the sentinel lymph node, thereby reducing the burden on the patient and making it possible to maintain favorable quality of life (QOL).

In order to identify a sentinel lymph node, a dye or radioactive colloid is administered into the periphery of the tumor, and then migration of the dye or radioactive colloid is monitored visually or with a radiation detector. Among conventionally used bioimaging dyes, patent blue, isosulfan blue and indocyanine green are used clinically as blue and green dyes capable of staining sentinel lymph nodes of the greatest importance in terms of the metastatic pathway (M. Kusano, ed., Overview of ICG Fluorescent Navigation Surgery, Intermedica, 2008). However, although imaging methods using patent blue, isosulfan blue or indocyanine green are simple, they diffuse in a relatively short period of time when administered to the body due to their small particle diameter, thereby resulting in difficulties in identification of the true target organ or tissue. Moreover, it is difficult to discriminate between stained lymph ducts and native venous vessels having blue or green color.

Microparticle dispersions containing radioisotopes such as 99mTc-S nanoparticles can be used for imaging of lymph flow and sentinel lymph nodes (Heiko Schroeder et al., Cancer Metastasis Rev (2006) 25:185-201). However, this approach has the problem of a considerable decrease in detection accuracy (attributable to shine through phenomenon) if the tracer administration site and detected site (such as a lymph node) are in close proximity, as well as the problem of requiring an operator qualified to work in radioactive controlled areas.

Another report revealed that, when liposomes having a particle diameter of 100 nm to 200 nm incorporating fluorescent quantum dots are introduced into a lymph flow, they accumulate in lymph nodes (Maoquan Chu et al., J. Nanopart. Res., DOI 10, 1007/s11051-009-9593-2). Since experiments evaluating the safety and toxicity of using fluorescent quantum particles in the body have not been adequately conducted, and since it is difficult to make accommodations for various particle diameters compatible with various target organs and tissues, bioimaging based on these particles has not been utilized universally in clinical settings.

Indocyanine green (ICG), represented by the following formula, is known to be a near-infrared fluorescent dye that is useful as a fluorescent probe for detecting sentinel lymph nodes.

[C1]

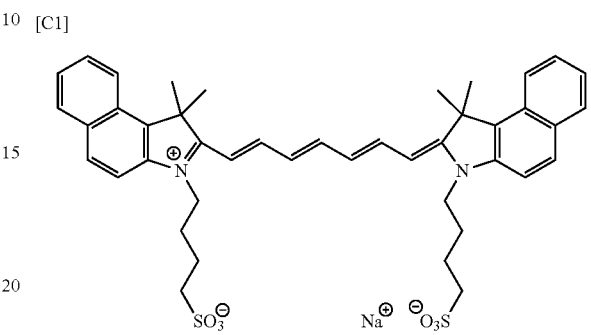

When a near-infrared fluorescent pigment is used as a dye, sentinel lymph nodes can be identified and distinguished from other tissue by irradiating with excitation light and detecting fluorescence in the near-infrared wavelength region. Moreover, since near-infrared rays are highly permeable in biological tissue, they enable sentinel lymph nodes to be identified at a depth of several centimeters from the skin surface. An example of a method for detecting sentinel lymph nodes using near-infrared fluorescent dye is disclosed in Japanese Patent Application Laid-open No. 2001-299676.

Indocyanine green forms a complex with lipoprotein and generates intense fluorescence in the near-infrared region when excited with light of a specific wavelength (see, for example, Yoneya et al., IOVS 39, 1286-1290, 1998). However, since the binding constant of indocyanine green and lipoprotein is low in comparison with the binding constant with other biomolecules, when a complex of indocyanine green and lipoprotein is introduced into the body, it will rapidly dissociate and can no longer be detected.

An aqueous solution of indocyanine green is reported to be selectively incorporated by rectal cancer when introduced through the anal (Shingo Noura et al., Ann. Surg. Oncol., DOI 10.1245/s10434-009-0711-2). Introduction of aqueous solutions of indocyanine green into organs finds limited applications because its tumor selectivity, diffusibility and retentivity are not consistent but are dependent on the organ where a tumor is located.

Moreover, when attempting to detect a lymph node using an aqueous solution of indocyanine green, the fluorescent signal cannot be monitored for a long time following administration of the dye due to rapid decrease in the fluorescence intensity, thus re-administration of the dye during surgery is often required. In addition, since indocyanine green has a short anchoring time in lymph nodes, it will flow out the lymph duct over time, thereby a fluorescent signal is also generated in lymph nodes farther downstream from the sentinel lymph node. Consequently, it is sometimes difficult to distinguish between the sentinal lymph node and other downstream lymph nodes during surgery.

Thus, there is a need for a fluorescent probe that is able to generate fluorescence of high intensity for a long period of time and have a long retention time in sentinel lymph nodes. Such a prove would allow for identifying sentinel lymph nodes with high accuracy, making it extremely useful in sentinel lymph node navigation surgery.

Reference documents cited in the description are as indicated below. All contents described in these documents are incorporated herein by reference.

Patent Document 1: Japanese Patent Application Laid-open No. 2001-299676

Non-Patent Document 1: Yoneya et al., IOVS 39, 1286-1290, 1998

DISCLOSURE OF THE INVENTION

An object of the present invention is to provide a fluorescent probe used as a near-infrared fluorescent imaging agent for lymph node imaging, and a fluorescent dye that is a constituent of the fluorescent probe and particularly suitable for that application.

The inventors of the present invention found that, when an indocyanine-based fluorescent dye is taken up into liposomes, in addition to increasing in fluorescence intensity, anchoring time in a sentinel lymph node becomes longer, thereby allowing the obtaining of a fluorescent probe useful for detection of sentinel lymph nodes. In addition, when the inventors of the present invention synthesized a large number of derivatives having a hexatriene skeletal structure similar to that of indocyanine green and investigated their fluorescence properties, it was found that a specific indocyanine green derivative has high fluorescence intensity and high affinity for lipids, and was found to be particularly suitable for use as a constituent of the fluorescent probe of the present invention.

Namely, the present invention provides a fluorescent probe for near-infrared fluorescent imaging in sentinel lymphadenography comprising a iposome containing a fluorescent dye having a hexatriene skeletal structure.

Preferably, the fluorescent dye having a hexatriene skeletal structure is a compound represented by chemical formula (I):

[C2]

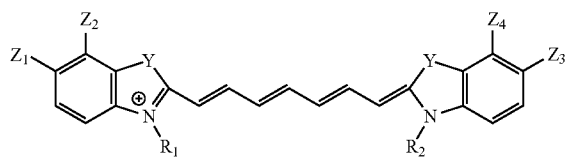

(I)

wherein, Y represents $-C(CH_3)_2-$, O or S, $Z_1$ and $Z_3$ represent hydrogen or $-OCH_3$, $Z_2$ and $Z_4$ represent hydrogen, or Z1 and Z2, and Z3 and Z4 may respectively together form a benzene ring fused with a ring to which they are bound, $R_1$ represents $-(CH_2)_n-SO_3$, $(CH_2)_n-X_1-(CH_2)_m-SO_3$, $-(CH_2)_n-COO$, $-(CH_2)_n-X_1-(CH_2)_m-COO$, $-(CH_2)_n-PO_4$, $-(CH_2)_n-X_1-(CH_2)_m-PO_4$, $-(CH_2)_n-OH(A)$, $-(CH_2)_n-X_1-(CH_2)_m-OH(A)$, $-(CH_2)_n-SH(A)$, $-(CH_2)_n-X_1-(CH_2)_m-SH(A)$, $-(CH_2)_n-NH_2(A)$, $-(CH_2)_n-X_1-(CH_2)_m-NH_2(A)$, $-(CH_2)_n-(CH_2CH_2O)_x-H(A)$, $-(CH_2)_n-X_1-(CH_2)_m-(CH_2CH_2O)_x-H(A)$, $-(CH_2)_n-CH_3(A)$, $-(CH_2)_n-X_1-(CH_2)_m-CH_3(A)$, $-(CH_2)_n-PO_4-(CH_2)_m-CH_3$, $-(CH_2)_n-PO_3(OC_lH_{2l+1})-(CH_2)_m-CH_3$, $-(CH_2)_n-CON(C_lH_{2l+1})-(CH_2)_m-CH_3(A)$, $-(CH_2)_n-N(C_lH_{2l+1})-(CH_2)_m-CH_3(A)$, $-(CH_2)_n-X_1-(CH_2)_p-CON(C_lH_{2l+1})-(CH_2)_m-CH_3(A)$ or $-(CH_2)_n-X_1-(CH_2)_p-N(C_lH_{2l+1})-(CH_2)_m-CH_3(A)$, where $X_1$ represents $-O-$, $-NH-$, $-S-$, $-SO_2-$, $-CH=CH-$, $-SO_2NH-$, $-NHSO_2-$, $-CONH-$, $-NHCO-$, $-CO-$, $-COO-$, $-OCO-$ or $-C_6H_4-$, A represents a monovalent anion in the form of a chloride ion, bromide ion or iodide ion, n and m represent an integer of 0 to 22, l represents an integer of 1 to 22, p represents an integer of 0 to 17, and x represents an integer of 2 to 2000, $R_2$ represents a group selected from the group consisting of the following groups:

[C3]

$-(CH_2)_nCH_3$  $-(CH_2)_nSH$  $-(CH_2)_nOH$  $-(CH_2)_nNH_2$ $-(CH_2)_n-SO_3$ (B)  $-(CH_2)_nCOO$ (B)

$-(CH_2)_n-PO_4$ (B)  $-(CH_2)_n-(CH_2O)_xH$ $-(CH_2)_nX_1(CH_2)_mCH_3$  $-(CH_2)_nX_1(CH_2)_mSH$ $-(CH_2)_nX_1(CH_2)_mOH$  $-(CH_2)_nX_1(CH_2)_mNH_2$ $-(CH_2)_nX_1(CH_2)_m-(CH_2CH_2O)_xH$ $-(CH_2)_nX_1(CH_2)_mCOO$ (B)  $-(CH_2)_nX_1(CH_2)_m-SO_3$ (B)

$-(CH_2)_nX_1(CH_2)_m-PO_4$ (B)  $-(CH_2)_nPO_4(CH_2)_mCH_3$(B)

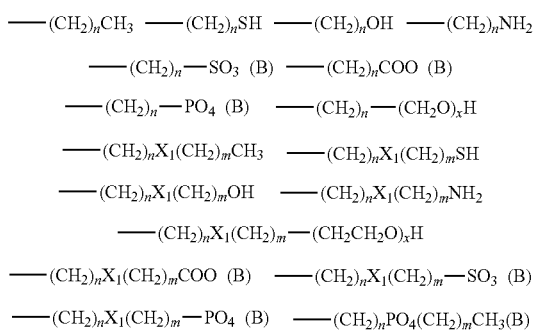

[C4]

$-(CH_2)_n-C\equiv C-(CH_2)_m-H$ $-(CH_2)_nX_1(CH_2)_p-C\equiv C-(CH_2)_m-H$ $-(CH_2)_n-N_3$  $-(CH_2)_nX_1(CH_2)_p-N_3$

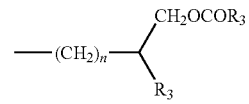

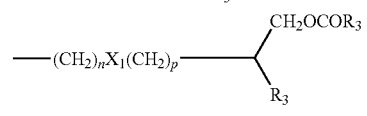

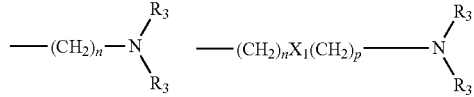

-continued

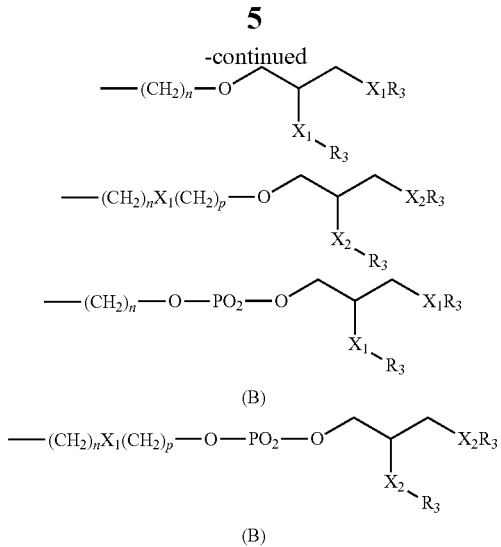

(B)

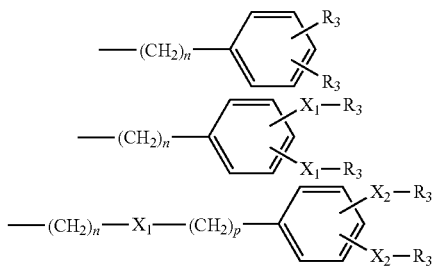

(B)

[C5]

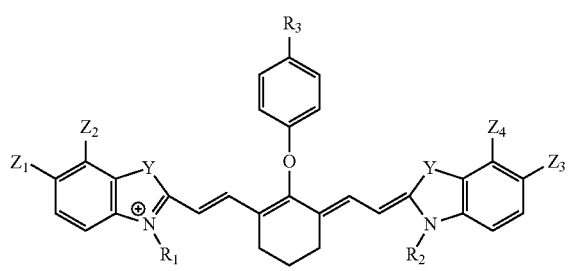

where, $X_1$ or $X_2$ represents —O—, —NH—, —S—, —SO$_2$—, —CH=CH—, —SO$_2$NH—, —NHSO$_2$—, —CONH—, —NHCO—, —CO—, —COO—, —OCO— or —C$_6$H$_4$—, and B represents a monovalent cation in the form of a hydrogen ion, lithium ion, sodium ion or potassium ion, and $R_3$ represents an alkane group, alkene group or alkyne group having 1 to 18 carbon atoms, n and m represent an integer of 0 to 22, l represents an integer of 1 to 22 and p represents an integer of 0 to 17; or a compound represented by chemical formula (II):

[C6]

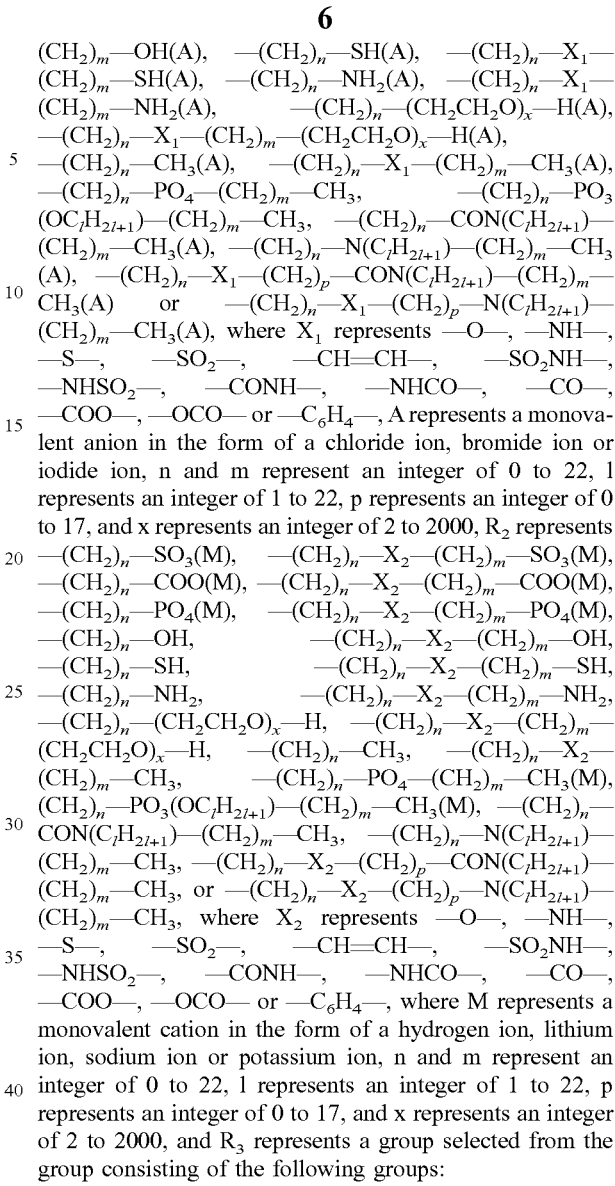

(II)

wherein, Y represents —C(CH$_3$)$_2$—, O or S, $Z_1$ and $Z_3$ represent hydrogen or —OCH$_3$, $Z_2$ and $Z_4$ represent hydrogen, or Z1 and Z2, and Z3 and Z4 may respectively together form a benzene ring fused with a ring to which they are bound, $R_1$ represents —(CH$_2$)$_n$—SO$_3$, —(CH$_2$)$_n$—X$_1$—(CH$_2$)$_m$—SO$_3$, —(CH$_2$)$_n$—COO, —(CH$_2$)$_n$—X$_1$—(CH$_2$)$_m$—COO, —(CH$_2$)$_n$—PO$_4$, —(CH$_2$)$_n$—X$_1$—(CH$_2$)$_m$—PO$_4$, —(CH$_2$)$_n$—OH(A), —(CH$_2$)$_n$—X$_1$—(CH$_2$)$_m$—OH(A), —(CH$_2$)$_n$—SH(A), —(CH$_2$)$_n$—X$_1$—(CH$_2$)$_m$—SH(A), —(CH$_2$)$_n$—NH$_2$(A), —(CH$_2$)$_n$—X$_1$—(CH$_2$)$_m$—NH$_2$(A), —(CH$_2$)$_n$—(CH$_2$CH$_2$O)$_x$—H(A), —(CH$_2$)$_n$—X$_1$—(CH$_2$)$_m$—(CH$_2$CH$_2$O)$_x$—H(A), —(CH$_2$)$_n$—CH$_3$(A), —(CH$_2$)$_n$—X$_1$—(CH$_2$)$_m$—CH$_3$(A), —(CH$_2$)$_n$—PO$_4$—(CH$_2$)$_m$—CH$_3$, —(CH$_2$)$_n$—PO$_3$(OC$_l$H$_{2l+1}$)—(CH$_2$)$_m$—CH$_3$, —(CH$_2$)$_n$—CON(C$_l$H$_{2l+1}$)—(CH$_2$)$_m$—CH$_3$(A), —(CH$_2$)$_n$—N(C$_l$H$_{2l+1}$)—(CH$_2$)$_m$—CH$_3$(A), —(CH$_2$)$_n$—X$_1$—(CH$_2$)$_p$—CON(C$_l$H$_{2l+1}$)—(CH$_2$)$_m$—CH$_3$(A) or —(CH$_2$)$_n$—X$_1$—(CH$_2$)$_p$—N(C$_l$H$_{2l+1}$)—(CH$_2$)$_m$—CH$_3$(A), where $X_1$ represents —O—, —NH—, —S—, —SO$_2$—, —CH=CH—, —SO$_2$NH—, —NHSO$_2$—, —CONH—, —NHCO—, —CO—, —COO—, —OCO— or —C$_6$H$_4$—, A represents a monovalent anion in the form of a chloride ion, bromide ion or iodide ion, n and m represent an integer of 0 to 22, l represents an integer of 1 to 22, p represents an integer of 0 to 17, and x represents an integer of 2 to 2000, $R_2$ represents —(CH$_2$)$_n$—SO$_3$(M), —(CH$_2$)$_n$—X$_2$—(CH$_2$)$_m$—SO$_3$(M), —(CH$_2$)$_n$—COO(M), —(CH$_2$)$_n$—X$_2$—(CH$_2$)$_m$—COO(M), —(CH$_2$)$_n$—PO$_4$(M), —(CH$_2$)$_n$—X$_2$—(CH$_2$)$_m$—PO$_4$(M), —(CH$_2$)$_n$—OH, —(CH$_2$)$_n$—X$_2$—(CH$_2$)$_m$—OH, —(CH$_2$)$_n$—SH, —(CH$_2$)$_n$—X$_2$—(CH$_2$)$_m$—SH, —(CH$_2$)$_n$—NH$_2$, —(CH$_2$)$_n$—X$_2$—(CH$_2$)$_m$—NH$_2$, —(CH$_2$)$_n$—(CH$_2$CH$_2$O)$_x$—H, —(CH$_2$)$_n$—X$_2$—(CH$_2$)$_m$—(CH$_2$CH$_2$O)$_x$—H, —(CH$_2$)$_n$—CH$_3$, —(CH$_2$)$_n$—X$_2$—(CH$_2$)$_m$—CH$_3$, —(CH$_2$)$_n$—PO$_4$—(CH$_2$)$_m$—CH$_3$(M), —(CH$_2$)$_n$—PO$_3$(OC$_l$H$_{2l+1}$)—(CH$_2$)$_m$—CH$_3$(M), —(CH$_2$)$_n$—CON(C$_l$H$_{2l+1}$)—(CH$_2$)$_m$—CH$_3$, —(CH$_2$)$_n$—N(C$_l$H$_{2l+1}$)—(CH$_2$)$_m$—CH$_3$, —(CH$_2$)$_n$—X$_2$—(CH$_2$)$_p$—CON(C$_l$H$_{2l+1}$)—(CH$_2$)$_m$—CH$_3$, or —(CH$_2$)$_n$—X$_2$—(CH$_2$)$_p$—N(C$_l$H$_{2l+1}$)—(CH$_2$)$_m$—CH$_3$, where $X_2$ represents —O—, —NH—, —S—, —SO$_2$—, —CH=CH—, —SO$_2$NH—, —NHSO$_2$—, —CONH—, —NHCO—, —CO—, —COO—, —OCO— or —C$_6$H$_4$—, where M represents a monovalent cation in the form of a hydrogen ion, lithium ion, sodium ion or potassium ion, n and m represent an integer of 0 to 22, l represents an integer of 1 to 22, p represents an integer of 0 to 17, and x represents an integer of 2 to 2000, and $R_3$ represents a group selected from the group consisting of the following groups:

[C7]

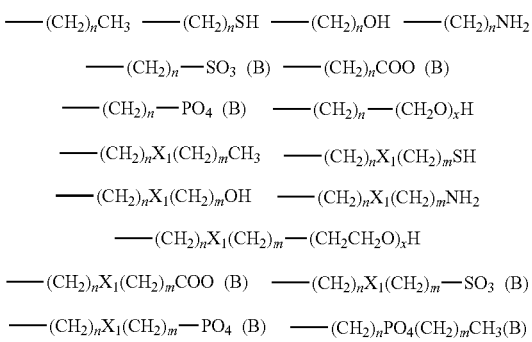

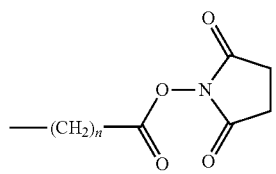

-continued

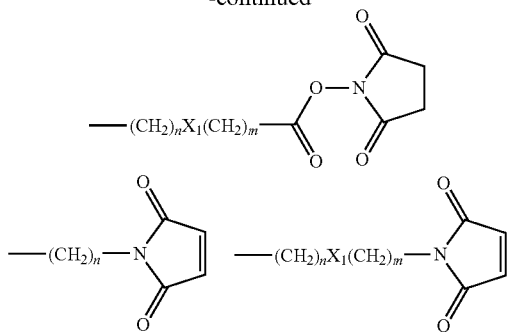

[C8]

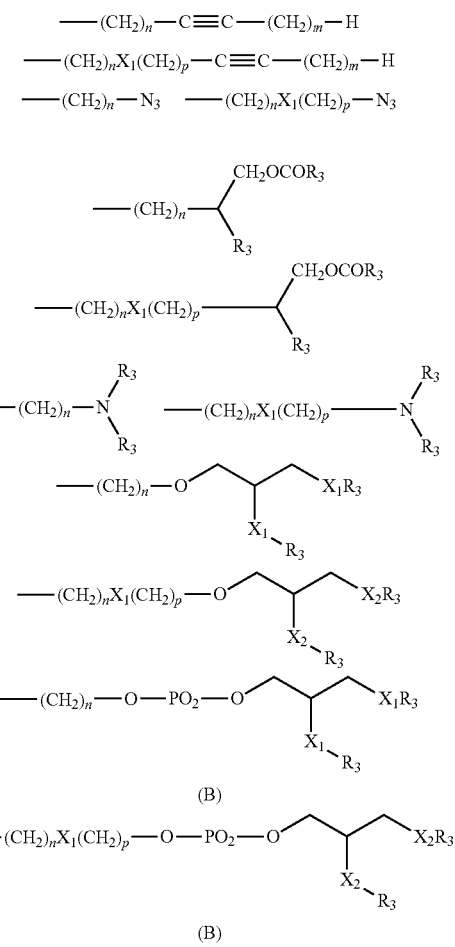

(B)

[C9]

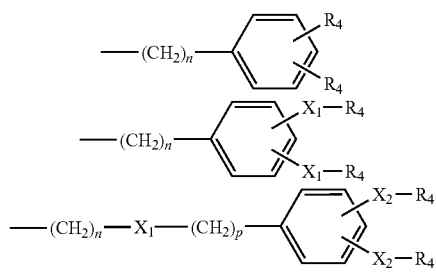

where, B represents a monovalent cation in the form of a hydrogen ion, lithium ion, sodium ion or potassium ion, $X_1$ or $X_2$ represent —O—, —NH—, —S—, —SO$_2$—, —CH=CH—, —SO$_2$NH—, —NHSO$_2$—, —CONH—, —NHCO—, —CO—, —COO—, —OCO— or —C$_6$H$_4$—, $R_4$ represents an alkane group, alkene group or alkyne group having 1 to 24 carbon atoms, n and m represent an integer of 0 to 22, l represents an integer of 1 to 22, and p represents an integer of 0 to 17.

In addition, the fluorescent dye having a hexatriene skeletal structure is a compound represented by chemical formula (III):

[C10]

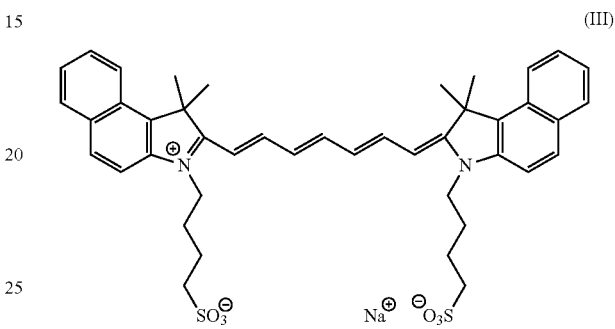

(III)

a compound represented by chemical formula (IV):

[C11]

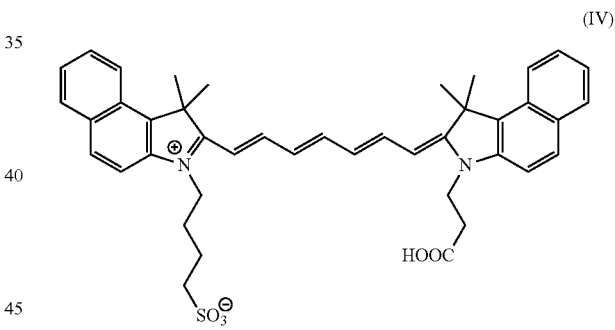

(IV)

a compound represented by chemical formula (V):

[C12]

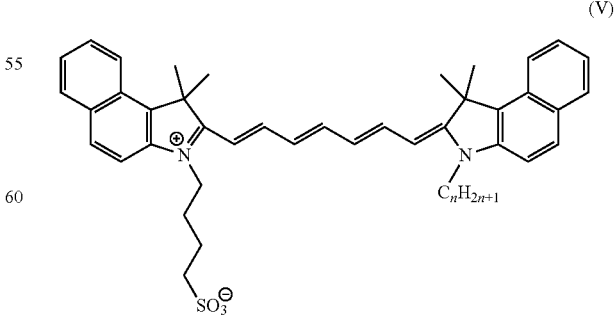

(V)

wherein, n represents an integer of 4 to 18, a compound represented by chemical formula (VI):

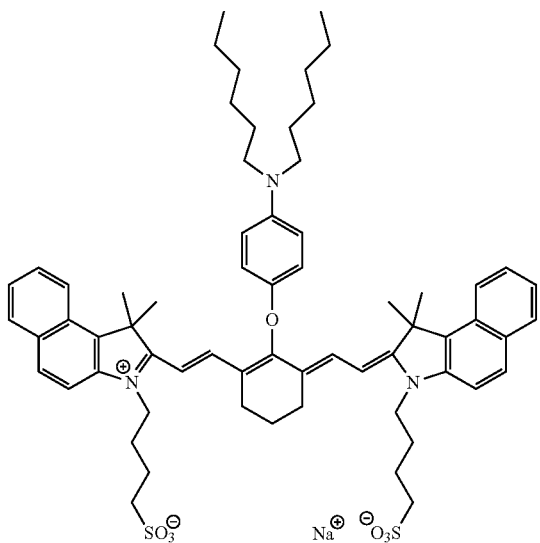

or, a compound represented by chemical formula (VII):

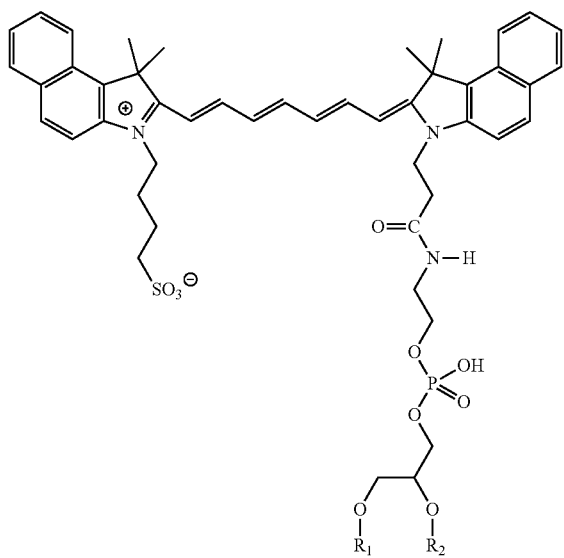

wherein, $R_1$ and $R_2$ represent a hexanoyl group, octanoyl group, decanoyl group, dodecanoyl group, tetradecanoyl group, hexadecanoyl group, octadecanoyl group, oleyl group, linoleyl group, linolenyl group, ricinoleyl group, geranyl group, geranylgeranyl group, farnesyl group, phytyl group or phytanyl group.

In the fluorescent probe for near-infrared fluorescent imaging in sentinel lymph node lymphadenography of the present invention, the particle diameter of the liposome preferably 100 nm to 300 nm and more preferably 150 nm to 250 nm.

In another aspect, the present invention provides a near-infrared fluorescent imaging agent comprising a compound represented by chemical formula (I):

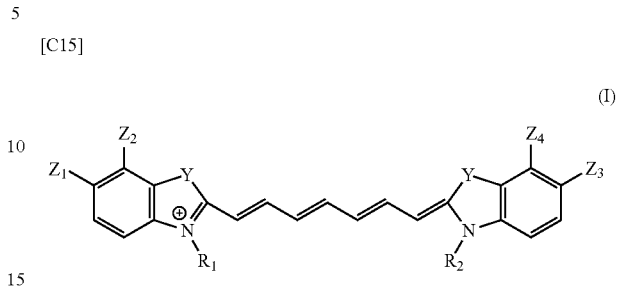

wherein, Y represents —$C(CH_3)_2$—, O or S, $Z_1$ and $Z_3$ represent hydrogen or —$OCH_3$, $Z_2$ and $Z_4$ represent hydrogen, or Z1 and Z2, and Z3 and Z4 may respectively together form a benzene ring fused with a ring to which they are bound, $R_1$ represents —$(CH_2)_n$—$SO_3$, —$(CH_2)_n$—$X_1$—$(CH_2)_m$—$SO_3$, —$(CH_2)$—$(CH_2)_n$—$X_1$—$(CH_2)_m$—COO, —$(CH_2)_n$—$PO_4$, —$(CH_2)_n$—$X_1$—$(CH_2)_m$—$PO_4$, $(CH_2)_n$—OH(A), —$(CH_2)_n$—$X_1$—$(CH_2)_m$—OH(A), —$(CH_2)_n$—SH (A), —$(CH_2)_n$—$X_1$—$(CH_2)_m$—SH(A), —$(CH_2)_n$—$NH_2$ (A), —$(CH_2)_n$—$X_1$—$(CH_2)_m$—$NH_2$(A), —$(CH_2)_n$—$(CH_2CH_2O)_x$—H(A), —$(CH_2)_n$—$X_1$—$(CH_2)_m$—$(CH_2CH_2O)_x$—H(A), —$(CH_2)_n$—$CH_3$(A), —$(CH_2)_n$—$X_1$—$(CH_2)_m$—$CH_3$(A), —$(CH_2)_n$—$PO_4$—$(CH_2)_m$—$CH_3$, —$(CH_2)_n$—$PO_3(OC_lH_{2l+1})$—$(CH_2)_m$—$CH_3$, —$(CH_2)_n$—$CON(C_lH_{2l+1})$—$(CH_2)_m$—$CH_3$(A), —$(CH_2)_n$—$N(C_lH_{2l+1})$—$(CH_2)_m$—$CH_3$(A), —$(CH_2)_n$—$X_1$—$(CH_2)_p$—$CON(C_lH_{2l+1})$—$(CH_2)_m$—$CH_3$(A) or —$(CH_2)_n$—$X_1$—$(CH_2)_p$—$N(C_lH_{2l+1})$—$(CH_2)_m$—$CH_3$(A), where $X_1$ represents —O—, —NH—, —S—, —$SO_2$—, —CH=CH—, —$SO_2$NH—, —$NHSO_2$—, —CONH—, —NHCO—, —CO—, —COO—, —OCO— or —$C_6H_4$—, A represents a monovalent anion in the form of a chloride ion, bromide ion or iodide ion, n and m represent an integer of 0 to 22, l represents an integer of 1 to 22, p represents an integer of 0 to 17, and x represents an integer of 2 to 2000, $R_2$ represents a group selected from the group consisting of the following groups:

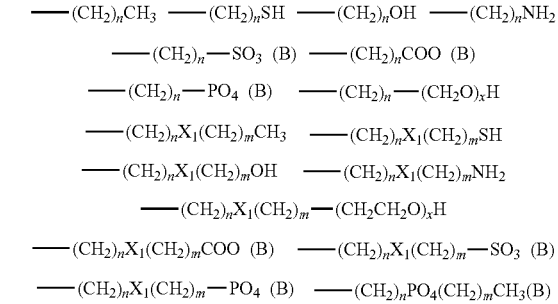

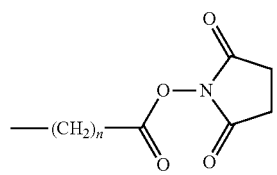

-continued

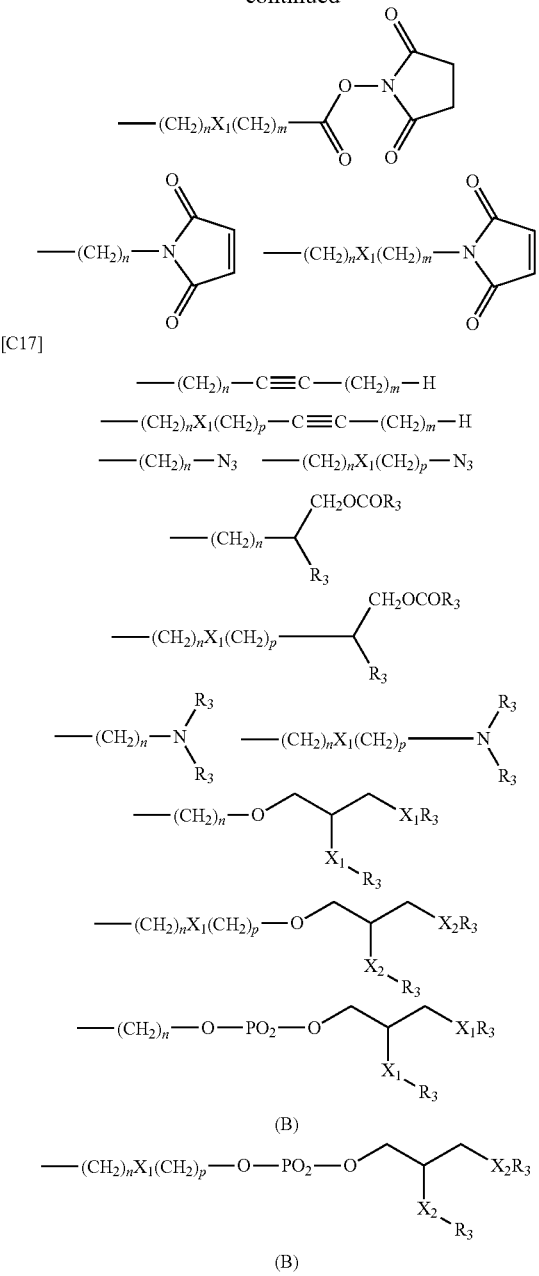

[C18]

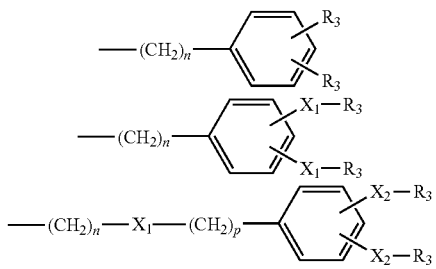

where, $X_1$ or $X_2$ represents —O—, —NH—, —S—, —$SO_2$—, —CH=CH—, —$SO_2NH$—, —$NHSO_2$—, —CONH—, —NHCO—, —CO—, —COO—, —OCO— or —$C_6H_4$—, and B represents a monovalent cation in the form of a hydrogen ion, lithium ion, sodium ion or potas-sium ion, and $R_3$ represents an alkane group, alkene group or alkyne group having 1 to 18 carbon atoms, n and m represent an integer of 0 to 22, l represents an integer of 1 to 22, and p represents an integer of 0 to 17; a compound represented by chemical formula (II):

[C19]

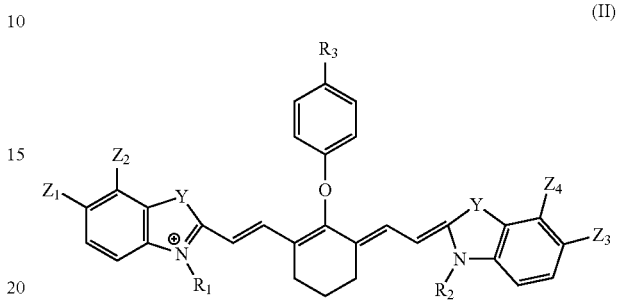

(II)

wherein, Y represents —$C(CH_3)_2$—, O or S, $Z_1$ and $Z_3$ represent hydrogen or —$OCH_3$, $Z_2$ and $Z_4$ represent hydrogen, or Z1 and Z2, and Z3 and Z4 may respectively together form a benzene ring fused with a ring to which they are bound, $R_1$ represents —$(CH_2)_n$—$SO_3$, —$(CH_2)_n$—$X_1$—$(CH_2)_m$—$SO_3$, —$(CH_2)_n$—COO, —$(CH_2)_n$—$X_1$—$(CH_2)_m$—COO, —$(CH_2)_n$—$PO_4$, —$(CH_2)_n$—$X_1$—$(CH_2)_m$—$PO_4$, $(CH_2)_n$OH(A), —$(CH_2)_n$—$X_1$—$(CH_2)_m$—OH(A), —$(CH_2)_n$—SH(A), —$(CH_2)_n$—$X_1$—$(CH_2)_m$—SH(A), —$(CH_2)_n$—$NH_2$(A), —$(CH_2)_n$—$X_1$—$(CH_2)_m$—$NH_2$(A), —$(CH_2)_n$—$(CH_2CH_2O)_x$—H(A), —$(CH_2)_n$—$X_1$—$(CH_2)_m$—$(CH_2CH_2O)_x$—H(A), —$(CH_2)_n$—$CH_3$(A), —$(CH_2)_n$—$X_1$—$(CH_2)_m$—$CH_3$(A), —$(CH_2)_n$—$PO_4$—$(CH_2)_m$—$CH_3$, —$(CH_2)_n$—$PO_3(OC_lH_{2l+1})$—$(CH_2)_m$—$CH_3$, —$(CH_2)_n$—$CON(C_lH_{2l+1})$—$(CH_2)_m$—$CH_3$(A), —$(CH_2)_n$—$N(CH_{2l+1})$—$(CH_2)_m$—$CH_3$(A), —$(CH_2)_n$—$X_1$—$(CH_2)_p$—$CON(C_lH_{2l+1})$—$(CH_2)_m$—$CH_3$(A) or —$(CH_2)_n$—$X_1$—$(CH_2)_p$—$N(C_lH_{2l+1})$—$(CH_2)_m$—$CH_3$(A), where $X_1$ represents —O—, —NH—, —S—, —$SO_2$—, —CH=CH—, —$SO_2NH$—, —$NHSO_2$—, —CONH—, —NHCO—, —CO—, —COO—, —OCO— or —$C_6H_4$—, A represents a monovalent anion in the form of a chloride ion, bromide ion or iodide ion, n and m represent an integer of 0 to 22, l represents an integer of 1 to 22, p represents an integer of 0 to 17, and x represents an integer of 2 to 2000, $R_2$ represents —$(CH_2)_n$—$SO_3(M)$, —$(CH_2)_n$—$X_2$—$(CH_2)_m$—$SO_3(M)$, —$(CH_2)_n$—COO(M), —$(CH_2)_n$—$X_2$—$(CH_2)_m$—COO(M), —$(CH_2)_n$—$PO_4(M)$, —$(CH_2)_n$—$X_2$—$(CH_2)_m$—$PO_4(M)$, $(CH_2)_n$—OH, —$(CH_2)_n$—$X_2$—$(CH_2)_m$—OH, —$(CH_2)_n$—SH, —$(CH_2)_n$—$X_2$—$(CH_2)_m$—SH, —$(CH_2)_n$—$NH_2$, —$(CH_2)_n$—$X_2$—$(CH_2)_m$—$NH_2$, —$(CH_2)_n$—$(CH_2CH_2O)_x$—H, —$(CH_2)_n$—$X_2$—$(CH_2)_m$—$(CH_2CH_2O)_x$—H, —$(CH_2)_n$—$CH_3$, —$(CH_2)_n$—$X_2$—$(CH_2)_m$—$CH_3$, —$(CH_2)_n$—$PO_4$—$(CH_2)_m$—$CH_3(M)$, —$(CH_2)_n$—$PO_3(OC_lH_{2l+1})$—$(CH_2)_m$—$CH_3(M)$, —$(CH_2)_n$—$CON(C_lH_{2l+1})$—$(CH_2)_m$—$CH_3$, —$(CH_2)_n$—N($C_lH_{2l+1}$)—$(CH_2)_m$—$CH_3$, —$(CH_2)_n$—$X_2$—$(CH_2)_p$—CON($C_lH_{2l+1}$)—$(CH_2)_m$—$CH_3$, or —$(CH_2)_n$—$X_2$—$(CH_2)_p$—N($C_lH_{2l+1}$)—$(CH_2)_m$—$CH_3$, where $X_2$ represents —O—, —NH—, —S—, —$SO_2$—, —CH=CH—, —$SO_2NH$—, —$NHSO_2$—, —CONH—, —NHCO—, —CO—, —COO—, —OCO— or —$C_6H_4$—, where M represents a monovalent cation in the form of a hydrogen ion, lithium ion, sodium ion or potassium ion, n and m represent an integer of 0 to 22, l represents an integer of 1 to 22, p represents an integer of 0 to 17, and x represents an integer of 2 to 2000, and $R_3$ represents a group selected from the group consisting of the following groups:

[C20]

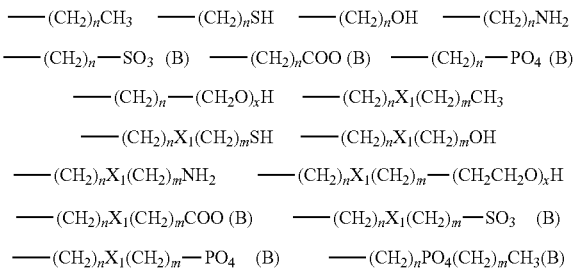

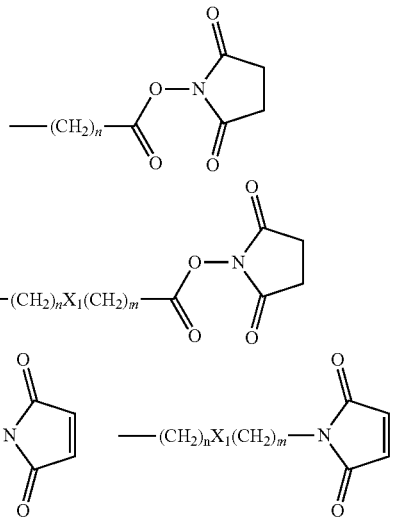

[C21]

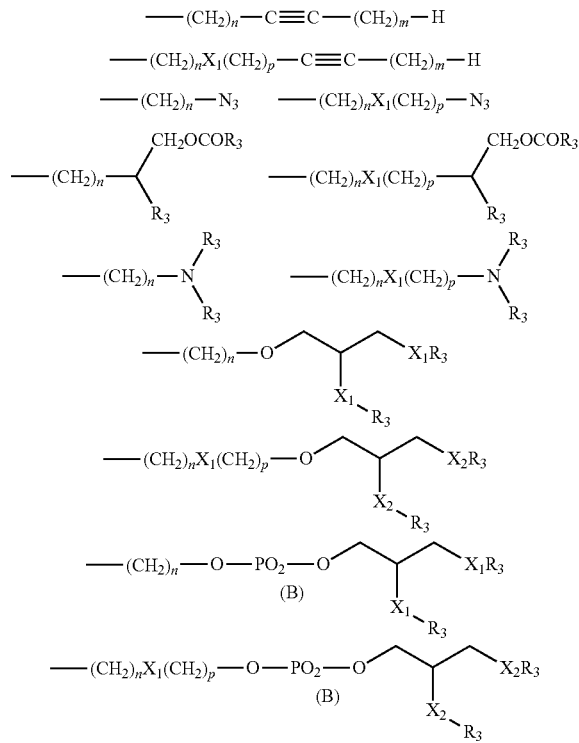

[C22]

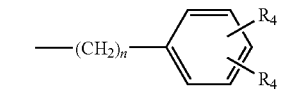

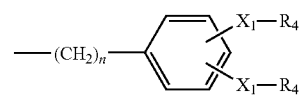

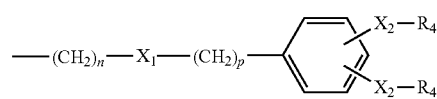

where, B represents a monovalent cation in the form of a hydrogen ion, lithium ion, sodium ion or potassium ion, $X_1$ or $X_2$ represent —O—, —NH—, —S—, —SO$_2$—, —CH=CH—, —SO$_2$NH—, —NHSO$_2$—, —CONH—, —NHCO—, —CO—, —COO—, —OCO— or —C$_6$H$_4$—, $R_4$ represents an alkane group, alkene group or alkyne group having 1 to 24 carbon atoms, n and m represent an integer of 0 to 22, l represents an integer of 1 to 22, and p represents an integer of 0 to 17; or a salt thereof.

In still another aspect, the present invention provides a near-infrared fluorescent imaging agent comprising a compound represented by chemical formula (III):

[C23]

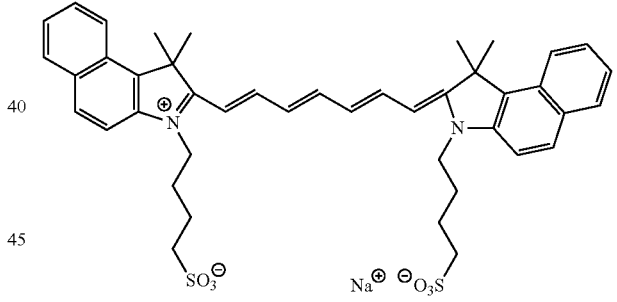

a compound represented by chemical formula (IV):

[C24]

(IV)

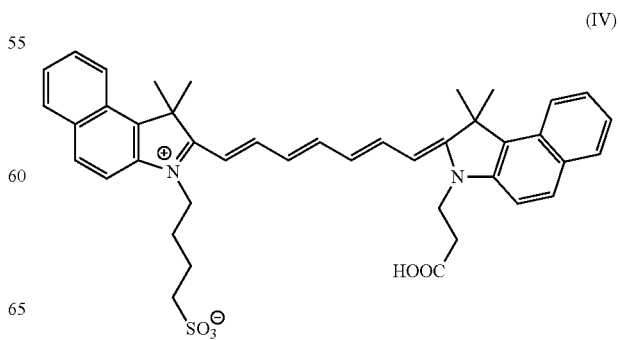

a compound represented by chemical formula (V):

[C25]

(V)

wherein, n represents an integer of 4 to 18,
a compound represented by chemical formula (VI):

[C26]

(VI)

or, a compound represented by chemical formula (VII):

[C27]

(VII)

wherein, $R_1$ and $R_2$ represent a hexanoyl group, octanoyl group, decanoyl group, dodecanoyl group, tetradecanoyl group, hexadecanoyl group, octadecanoyl group, oleyl group, linoleyl group, linolenyl group, ricinoleyl group, geranyl group, geranylgeranyl group, farnesyl group, phytyl group or phytanyl group.

In still another aspect, the present invention provides a method for identifying a sentinel lymph node comprising detecting fluorescence generated from the fluorescent probe of the present invention.

In still another aspect, the present invention provides a compound represented by the chemical formula (I), (II), (IV), (V), (VI) or (VII).

BRIEF DESCRIPTION OF THE DRAWINGS

FIG. 1 shows a schematic diagram of a fluorescent probe for lymph node imaging.
FIG. 2 shows the fluorescence properties of an ICG-8 fluorescent probe.
FIG. 3A shows the fluorescence properties of various types of fluorescent probes.
FIG. 3B shows the fluorescence properties of various types of fluorescent probes.
FIG. 4 shows the particle diameter distribution of a fluorescent probe.
FIG. 5 shows the in vivo fluorescence detectability of a fluorescent probe.
FIG. 6 shows the anchoring property of a fluorescent probe in a mouse popliteal lymph node.
FIG. 7 shows the anchoring property of a fluorescent probe in a porcine sigmoid lymph node.
FIG. 8 shows the anchoring property of a fluorescent probe in a porcine subpyloric lymph node (left: camera image, fluorescent image).

PREFERRED EMBODIMENTS OF THE INVENTION

Near-Infrared Fluorescent Dye

The near-infrared fluorescent imaging agent of the present invention comprises an indocyanine-based fluorescent dye and a liposome. Examples of the indocyanine-based fluorescent dyes that can be used in the present invention include a compound represented by chemical formula (I):

[C28]

(I)

wherein, Y represents —C(CH$_3$)$_2$—, O or S, $Z_1$ and $Z_3$ represent hydrogen or —OCH$_3$, $Z_2$ and $Z_4$ represent hydrogen, or Z1 and Z2, and Z3 and Z4 may respectively together form a benzene ring fused with a ring to which they are bound, $R_1$ represents —(CH$_2$)$_n$—SO$_3$, —(CH$_2$)$_n$—X$_1$— (CH$_2$)$_m$—SO$_3$, —(CH$_2$)$_n$—COO, —(CH$_2$)$_n$—X$_1$— (CH$_2$)$_m$—COO, —(CH$_2$)$_n$—PO$_4$, —(CH$_2$)$_n$—X$_1$— (CH$_2$)$_m$—PO$_4$, —(CH$_2$)$_n$—OH(A), —(CH$_2$)$_n$—X$_1$— (CH$_2$)$_m$—OH(A), —(CH$_2$)$_n$—SH(A), —(CH$_2$)$_n$—X$_1$— (CH$_2$)$_m$—SH(A), —(CH$_2$)$_n$—NH$_2$(A), —(CH$_2$)$_n$—X$_1$—

$-(CH_2)_m-NH_2(A)$, $-(CH_2)_n-(CH_2CH_2O)_x-H(A)$, $-(CH_2)_n-X_1-(CH_2)_m-(CH_2CH_2O)_x-H(A)$, $-(CH_2)_n-CH_3(A)$, $-(CH_2)_n-X_1-(CH_2)_m-CH_3(A)$, $-(CH_2)_n-PO_4-(CH_2)_m-CH_3$, $-(CH_2)_n-PO_3(OC_lH_{2l+1})-(CH_2)_m-CH_3$, $-(CH_2)_n-CON(C_lH_{2l+1})-(CH_2)_m-CH_3(A)$, $-(CH_2)_n-N(C_lH_{2l+1})-(CH_2)_m-CH_3(A)$, $-(CH_2)_n-X_1-(CH_2)_p-CON(C_lH_{2l+1})-(CH_2)_m-CH_3(A)$ or $-(CH_2)_n-X_1-(CH_2)_p-N(C_lH_{2l+1})-(CH_2)_m-CH_3(A)$, where $X_1$ represents $-O-$, $-NH-$, $-S-$, $-SO_2-$, $-CH=CH-$, $-SO_2NH-$, $-NHSO_2-$, $-CONH-$, $-NHCO-$, $-CO-$, $-COO-$, $-OCO-$ or $-C_6H_4-$, A represents a monovalent anion in the form of a chloride ion, bromide ion or iodide ion, n and m represent an integer of 0 to 22, l represents an integer of 1 to 22, p represents an integer of 0 to 17, and x represents an integer of 2 to 2000, $R_2$ represents a group selected from the group consisting of the following groups:

[C29]

$-(CH_2)_nCH_3$  $-(CH_2)_nSH$  $-(CH_2)_nOH$  $-(CH_2)_nNH_2$
$-(CH_2)_n-SO_3$ (B)  $-(CH_2)_nCOO$ (B)  $-(CH_2)_n-PO_4$ (B)
$-(CH_2)_n-(CH_2O)_xH$  $-(CH_2)_nX_1(CH_2)_mCH_3$
$-(CH_2)_nX_1(CH_2)_mSH$  $-(CH_2)_nX_1(CH_2)_mOH$
$-(CH_2)_nX_1(CH_2)_mNH_2$  $-(CH_2)_nX_1(CH_2)_m-(CH_2CH_2O)_xH$
$-(CH_2)_nX_1(CH_2)_mCOO$ (B)  $-(CH_2)_nX_1(CH_2)_m-SO_3$ (B)
$-(CH_2)_nX_1(CH_2)_m-PO_4$ (B)  $-(CH_2)_nPO_4(CH_2)_mCH_3$(B)

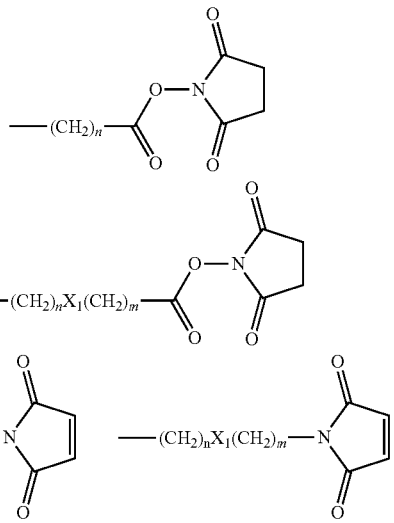

[C30]

$-(CH_2)_n-C\equiv C-(CH_2)_m-H$
$-(CH_2)_nX_1(CH_2)_p-C\equiv C-(CH_2)_m-H$
$-(CH_2)_n-N_3$  $-(CH_2)_nX_1(CH_2)_p-N_3$

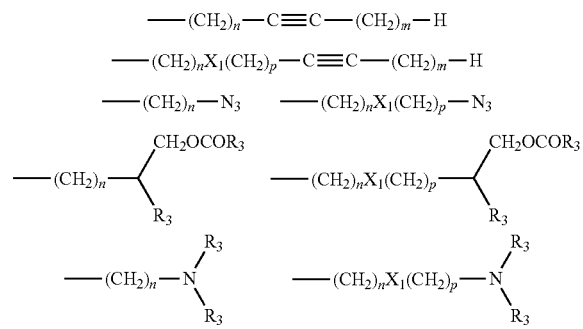

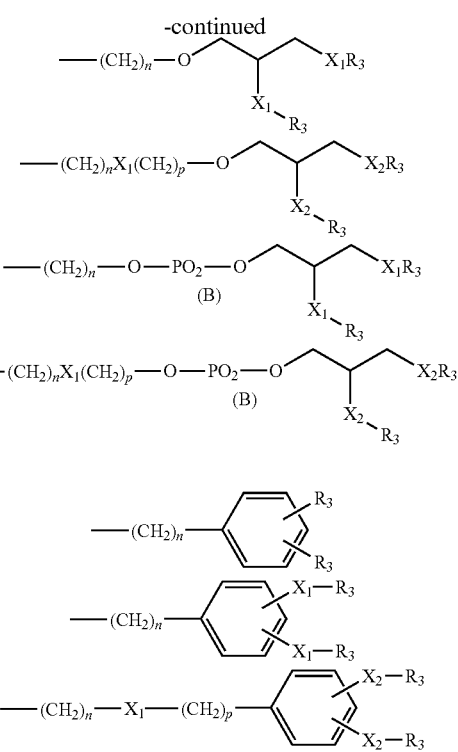

[C31]

where, $X_1$ or $X_2$ represents $-O-$, $-NH-$, $-S-$, $-SO_2-$, $-CH=CH-$, $-SO_2NH-$, $-NHSO_2-$, $-CONH-$, $-NHCO-$, $-CO-$, $-COO-$, $-OCO-$ or $-C_6H_4-$, and B represents a monovalent cation in the form of a hydrogen ion, lithium ion, sodium ion or potassium ion, and $R_3$ represents an alkane group, alkene group or alkyne group having 1 to 18 carbon atoms, n and m represent an integer of 0 to 22, l represents an integer of 1 to 22 and p represents an integer of 0 to 17; or a compound represented by chemical formula (II):

[C32]

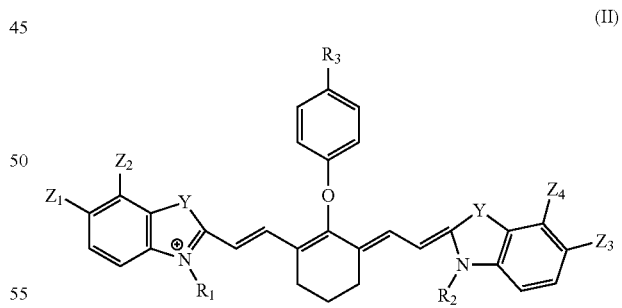

(II)

wherein, Y represents $-C(CH_3)_2-$, O or S, $Z_1$ and $Z_3$ represent hydrogen or $-OCH_3$, $Z_2$ and $Z_4$ represent hydrogen, or Z1 and Z2, and Z3 and Z4 may respectively together form a benzene ring fused with a ring to which they are bound, $R_1$ represents $-(CH_2)_n-SO_3$, $-(CH_2)_n-X_1-(CH_2)_m-SO_3$, $-(CH_2)_n-COO$, $-(CH_2)_n-X_1-(CH_2)_m-COO$, $-(CH_2)_n-PO_4$, $-(CH_2)_n-X_1-(CH_2)_m-PO_4$, $-(CH_2)_n-OH(A)$, $-(CH_2)_n-X_1-(CH_2)_m-OH(A)$, $-(CH_2)_n-SH(A)$, $-(CH_2)_n-X_1-(CH_2)_m-SH(A)$, $-(CH_2)_n-NH_2(A)$, $-(CH_2)_n-X_1-$ —(CH$_2$)$_m$—NH$_2$(A), —(CH$_2$)$_n$—(CH$_2$CH$_2$O)$_x$—H(A), —(CH$_2$)$_n$—X$_1$—(CH$_2$)$_m$—(CH$_2$CH$_2$O)$_x$—H(A), —(CH$_2$)$_n$—CH$_3$(A), —(CH$_2$)$_n$—X$_1$—(CH$_2$)$_m$—CH$_3$(A), —(CH$_2$)$_n$—PO$_4$—(CH$_2$)$_m$—CH$_3$, —(CH$_2$)$_n$—PO$_3$(OC$_l$H$_{2l+1}$)—(CH$_2$)$_m$—CH$_3$, —(CH$_2$)$_n$—CON(C$_l$H$_{2l+1}$)—(CH$_2$)$_m$—CH$_3$(A), —(CH$_2$)$_n$—N(C$_l$H$_{2l+1}$)—(CH$_2$)$_m$—CH$_3$(A), —(CH$_2$)$_n$—X$_1$—(CH$_2$)$_p$—CON(C$_l$H$_{2l+1}$)—(CH$_2$)$_m$—CH$_3$(A) or —(CH$_2$)$_n$—X$_1$—(CH$_2$)$_p$—N(C$_l$H$_{2l+1}$)—(CH$_2$)$_m$—CH$_3$(A), where X$_1$ represents —O—, —NH—, —S—, —SO$_2$—, —CH=CH—, —SO$_2$NH—, —NHSO$_2$—, —CONH—, —NHCO—, —CO—, —COO—, —OCO— or —C$_6$H$_4$—, A represents a monovalent anion in the form of a chloride ion, bromide ion or iodide ion, n and m represent an integer of 0 to 22, l represents an integer of 1 to 22, p represents an integer of 0 to 17, and x represents an integer of 2 to 2000, R$_2$ represents —(CH$_2$)$_n$—SO$_3$(M), —(CH$_2$)$_n$—X$_2$—(CH$_2$)$_m$—SO$_3$(M), —(CH$_2$)$_n$—COO(M), —(CH$_2$)$_n$—X$_2$—(CH$_2$)$_m$—COO(M), —(CH$_2$)$_n$—PO$_4$(M), —(CH$_2$)$_n$—X$_2$—(CH$_2$)$_m$—PO$_4$(M), —(CH$_2$)$_n$—OH, —(CH$_2$)$_n$—X$_2$—(CH$_2$)$_m$—OH, —(CH$_2$)$_n$—SH, —(CH$_2$)$_n$—X$_2$—(CH$_2$)$_m$—SH, —(CH$_2$)$_n$—NH$_2$, —(CH$_2$)$_n$—X$_2$—(CH$_2$)$_m$—NH$_2$, —(CH$_2$)$_n$—(CH$_2$CH$_2$O)$_x$—H, —(CH$_2$)$_n$—X$_2$—(CH$_2$)$_m$—(CH$_2$CH$_2$O)$_x$—H, —(CH$_2$)$_n$—CH$_3$, —(CH$_2$)$_n$—X$_2$—(CH$_2$)$_m$—CH$_3$, —(CH$_2$)$_n$—PO$_4$—(CH$_2$)$_m$—CH$_3$(M), —(CH$_2$)$_n$—PO$_3$(OC$_l$H$_{2l+1}$)—(CH$_2$)$_m$—CH$_3$(M), —(CH$_2$)$_n$—CON(C$_l$H$_{2l+1}$)—(CH$_2$)$_m$—CH$_3$, —(CH$_2$)$_n$—N(C$_l$H$_{2l+1}$)—(CH$_2$)$_m$—CH$_3$, —(CH$_2$)$_n$—X$_2$—(CH$_2$)$_p$—CON(C$_l$H$_{2l+1}$)—(CH$_2$)$_m$—CH$_3$, or —(CH$_2$)$_n$—X$_2$—(CH$_2$)$_p$—N(C$_l$H$_{2l+1}$)—(CH$_2$)$_m$—CH$_3$, where X$_2$ represents —O—, —NH—, —S—, —SO$_2$—, —CH=CH—, —SO$_2$NH—, —NHSO$_2$—, —CONH—, —NHCO—, —CO—, —COO—, —OCO— or —C$_6$H$_4$—, where M represents a monovalent cation in the form of a hydrogen ion, lithium ion, sodium ion or potassium ion, n and m represent an integer of 0 to 22, l represents an integer of 1 to 22, p represents an integer of 0 to 17, and x represents an integer of 2 to 2000, and R$_3$ represents a group selected from the group consisting of the following groups:

[C33]

—(CH$_2$)$_n$CH$_3$    —(CH$_2$)$_n$SH    —(CH$_2$)$_n$OH    —(CH$_2$)$_n$NH$_2$

—(CH$_2$)$_n$—SO$_3$ (B)    —(CH$_2$)$_n$COO (B)    —(CH$_2$)$_n$—PO$_4$ (B)

—(CH$_2$)$_n$—(CH$_2$O)$_x$H    —(CH$_2$)$_n$X$_1$(CH$_2$)$_m$CH$_3$

—(CH$_2$)$_n$X$_1$(CH$_2$)$_m$SH    —(CH$_2$)$_n$X$_1$(CH$_2$)$_m$OH

—(CH$_2$)$_n$X$_1$(CH$_2$)$_m$NH$_2$    —(CH$_2$)$_n$X$_1$(CH$_2$)$_m$—(CH$_2$CH$_2$O)$_x$H

—(CH$_2$)$_n$X$_1$(CH$_2$)$_m$COO (B)    —(CH$_2$)$_n$X$_1$(CH$_2$)$_m$—SO$_3$ (B)

—(CH$_2$)$_n$X$_1$(CH$_2$)$_m$—PO$_4$ (B)    —(CH$_2$)$_n$PO$_4$(CH$_2$)$_m$CH$_3$(B)

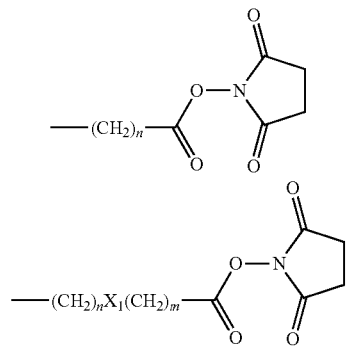

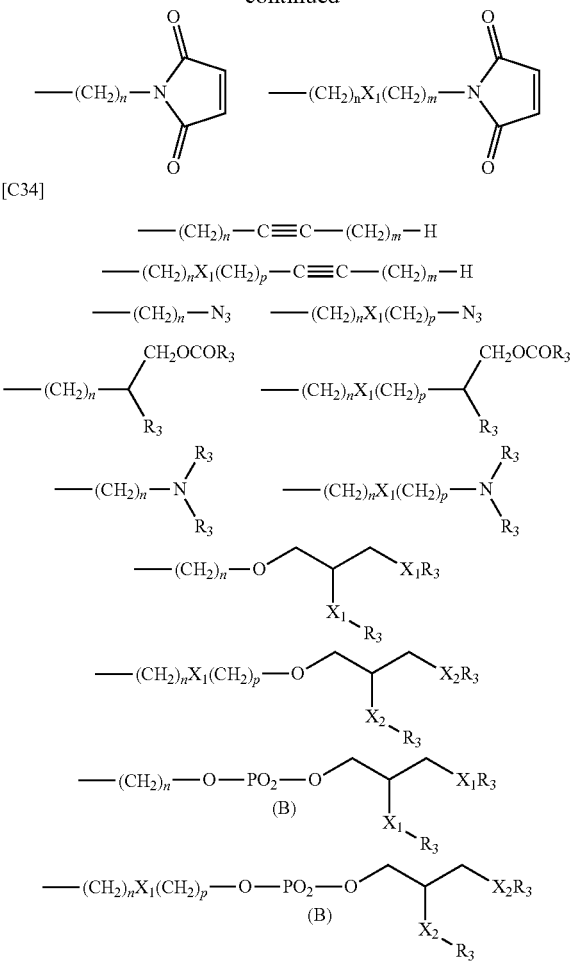

[C34]

[C35]

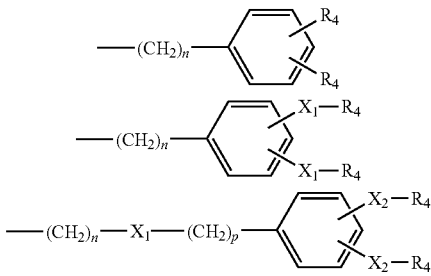

where, B represents a monovalent cation in the form of a hydrogen ion, lithium ion, sodium ion or potassium ion, X$_1$ or X$_2$ represents —O—, —NH—, —S—, —SO$_2$—, —CH=CH—, —SO$_2$NH—, —NHSO$_2$—, —CONH—, —NHCO—, —CO—, —COO—, —OCO— or —C$_6$H$_4$—, R$_4$ represents an alkane group, alkene group or alkyne group having 1 to 24 carbon atoms, n and m represent an integer of 0 to 22, l represents an integer of 1 to 22, and p represents an integer of 0 to 17.

These compounds can be easily synthesized using methods commonly known in the art, examples include those disclosed in Japanese Patent Application Laid-open No. H09-124599, WO 1995/007888, Japanese Patent Application Laid-open No. H03-171136 and J. Org. Chem., 60, 2391 (1995). Among these compounds, indocyanine green (ICG):

[C36]

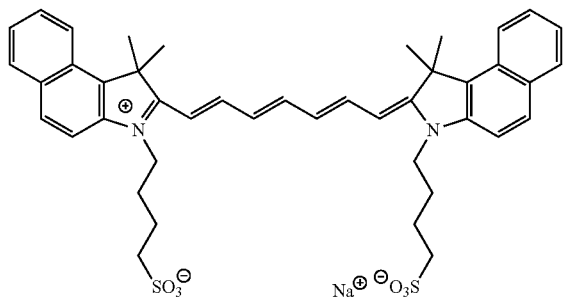

is already commercially available as a contrast agent, and can be preferably used in the present invention.

The inventors have synthesized a large number of derivatives having a hexatriene skeletal structure similar to that of indocyanine green and investigated their fluorescence properties. It was found that, in particular, the following compounds have high fluorescence intensity, and have high stability on a liposome lipid bilayer membrane: [4-(2-((1E,3E,5E,7E)-7-(3-(2-carboxyethyl)-1,1-dimethyl-1H-benzo[e]indol-2-(3H)-ylidene) hepta-1,3,5-trienyl)-1,1-dimethyl-1H-benzo[e]indolium-3-yl) butane-1-sulfonic acid] (referred to as ICG-6 herein):

[C37]

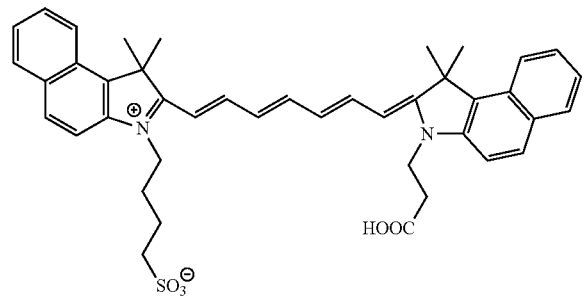

the compound [4(2-((1E,3E,5E,7E)-7-(1,1-dimethyl-3-octadecyl-1H-benzo[e]indol-2(3H)-ylidene)hepta-1,3,5-trienyl)-1,1-dimethyl-1H-benzo[e]indolium-3-yl)butane-1-sulfonic acid] (referred to as ICG-8 herein):

[C38]

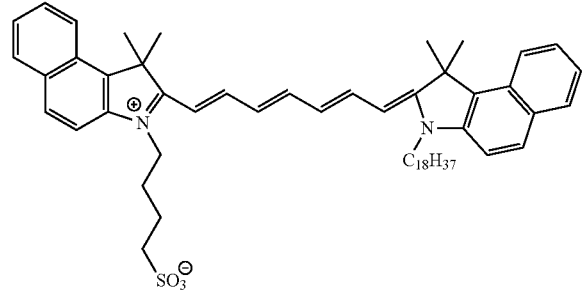

the compound sodium [4-(2-((E)-2-((E)-2-(4-(dihexyamino)phenoxy)-3-((E)-2-(1,1-dimethyl-3-(4-sulfonatebutyl)-1H-benzo[e]indol-2(3H)-ylidene)ethylidene) cyclohexenyl)vinyl)-1,1-dimethyl-1H-benzo[e]indolium-3-yl) butane-1-sulfonate] (referred to as ICG-9 herein):

[C39]

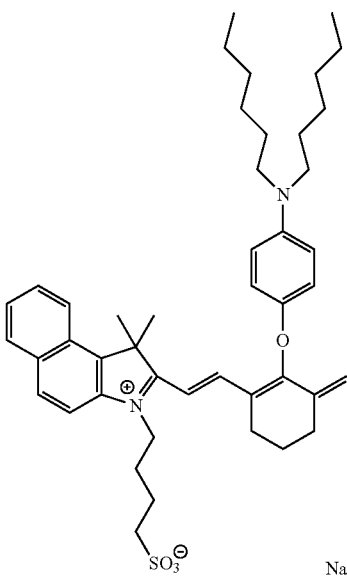

a compound represented by the chemical formula:

[C40]

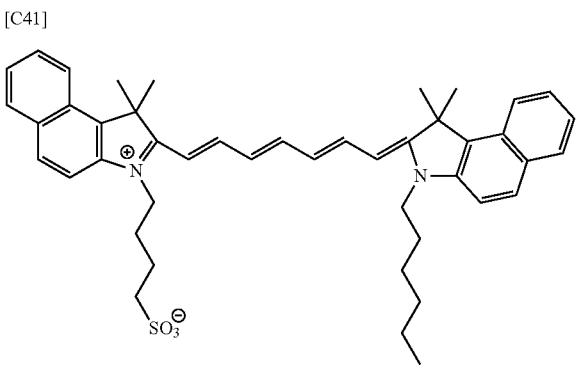

(referred to as ICG-8-C4 herein), or a compound represented by the chemical formula:

[C41]

(referred to as ICG-8-C6 herein), or a compound represented by the chemical formula:

[C42]

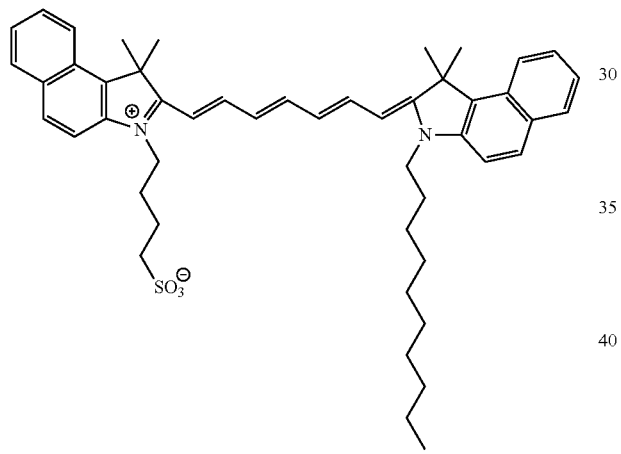

(referred to as ICG-8-C8 herein), or a compound represented by the chemical formula:

[C43]

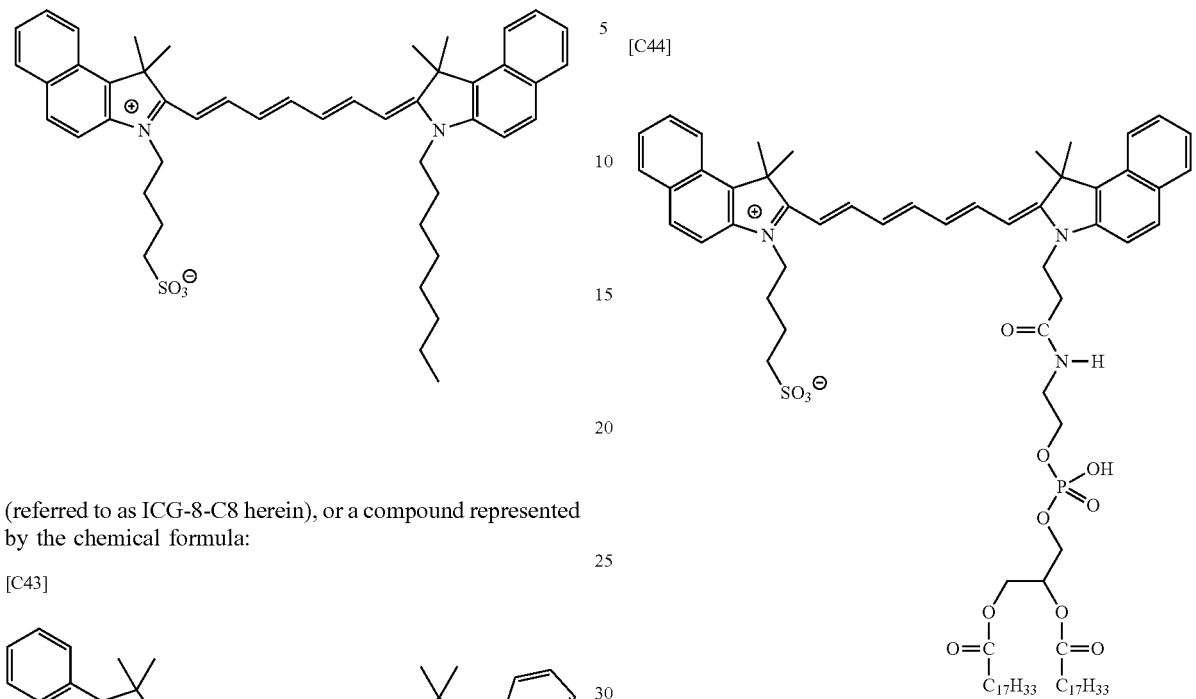

(referred to as ICG-8-C10 herein), or a compound represented by the chemical formula:

[C44]

(referred to as ICG-11-DOPE herein). These compounds are particularly suitable for use in the near-infrared fluorescent imaging agent of the present invention.

The novel fluorescent dyes ICG-6 and ICG-8 used in the near-infrared fluorescent imaging agent of the present invention can be synthesized according to the following scheme in accordance with the descriptions of WO 1995/007888 and Japanese Patent Application Laid-open No. H09-124599.

[C45]

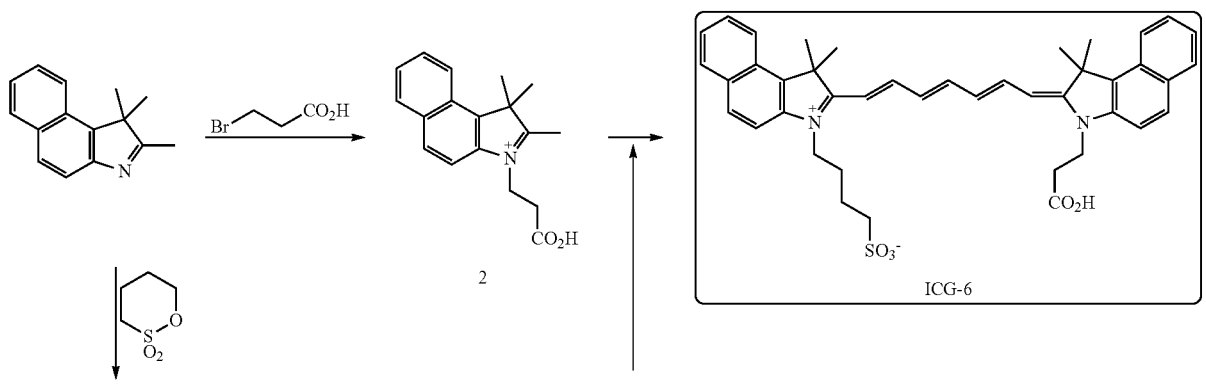

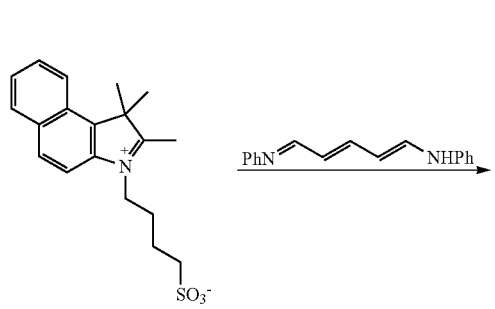
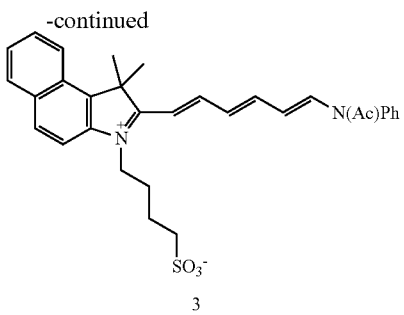
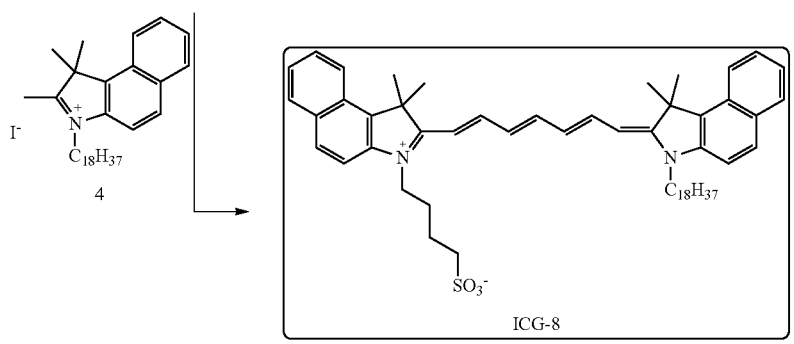

Commercially available 2,3,3-trimethyl-4,5-benzo-3H-indole is reacted with 1,4-butanesultone to form one of the units indicated in the chemical formula in the form of 2,3,3-trimethyl-1-(sulfobutyl)-4,5-benzoindole (1), and then coupled to a hexatriene chain by reacting with glutaconaldehyde dianil hydrochloride to obtain 2-(6-acetoanilido-1,3,5-hexatrienyl)-3,3-dimethyl-1-(sulfobutyl)-4,5-benzo[e]indole (3). The other unit indicated in the chemical formula of ICG-6 in the form of 2,3,3-trimethyl-1-(2-carboxyethyl)-4,5-benzoindole (2) can be obtained by reacting 2,3,3-trimethyl-4,5-benzo-3H-indole with a halogenated propionic acid. ICG-6 can be obtained by coupling these two units in the presence of pyridine.

The other unit indicated in the chemical formula of ICG-8 in the form of 1-octadecyl-2,3,3-trimethyl-4,5-benzo[e]indole (4) can be obtained by alkylating 2,3,3-trimethyl-4,5-benzo-3H-indole with a halogenated octadecane, which is then coupled to 2-(6-acetoanilido-1,3,5-hexatrienyl)-3,3-dimethyl-1-(sulfobutyl)-4,5-benzo[e]indole (3) to obtain ICG-8.

The novel fluorescent dye ICG-9 used in the near-infrared fluorescent imaging agent of the present invention can be synthesized according to the following scheme in accordance with the descriptions of Japanese Patent Application Laid-open No. H03-171136 and J. Org. Chem., 60, 2391 (1995).

[C46]

A

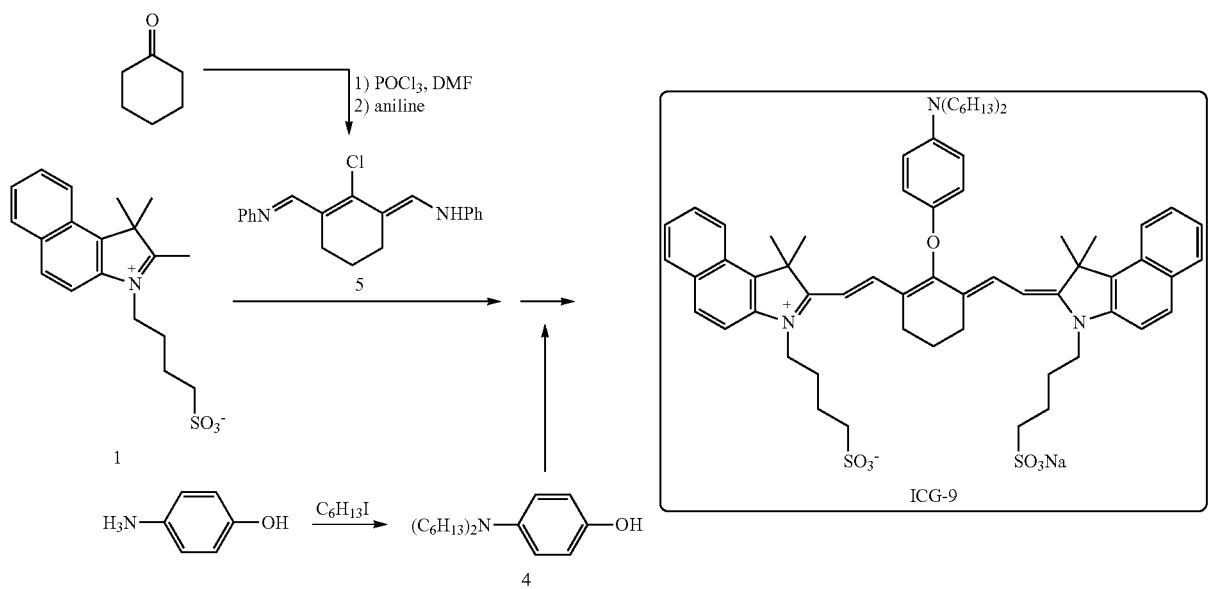

3-chloro-2,4-trimethylene glutaconaldehyde dianil hydrochloride (5), which forms the triene skeleton, can be obtained by converting cyclohexanone to an aldehyde using phosphorous oxychloride and coupling the aldenyde with aniline. A cyanine dye can be obtained by coupling the compound (5) with 2,3,3-trimethyl-1-(sulfobutyl)-4,5-benzoindole (1) unit formed as described above in the presence of triethylamine, methanol and acetic anhydride. The pendant group on the triene skeleton in the form of p-(di-n-hexylamino)phenol (4) is obtained by alkylating p-aminophenol with an alkyl halide, which is then reacted with sodium hydride to form a sodium phenoxide and coupled with the cyanine dye to obtain ICG-9.

The phospholipid-modified fluorescent dye ICG-11-DOPE used in the near-infrared fluorescent imaging agent of the present invention, can be synthesized according to the following scheme from a commercially available dioleoyl-phosphatidylethanolamine (Coatsome ME-8181).

agent of the present invention are able to generate fluorescence at wavelengths in the near-infrared region, and have high molar extinction coefficients similar to that of ICG. The molar extinction coefficients of the fluorescent dyes are shown in Table 1.

TABLE 1

| Name | λ max (EtOH) | Molar Extinction Coefficient (ε) |
|---|---|---|
| ICG (commercially available*) | 787 nm | $1.47 \times 10^5$ |
| ICG-6 | 786 nm | $1.86 \times 10^5$ |
| ICG-8 | 787 nm | $2.30 \times 10^5$ |
| ICG-9 | 810 nm | $1.24 \times 10^5$ |
| ICG-8-C4 | 787 nm | $2.52 \times 10^5$ |
| ICG-8-C6 | 787 nm | $2.34 \times 10^5$ |
| ICG-8-C8 | 788 nm | $2.63 \times 10^5$ |

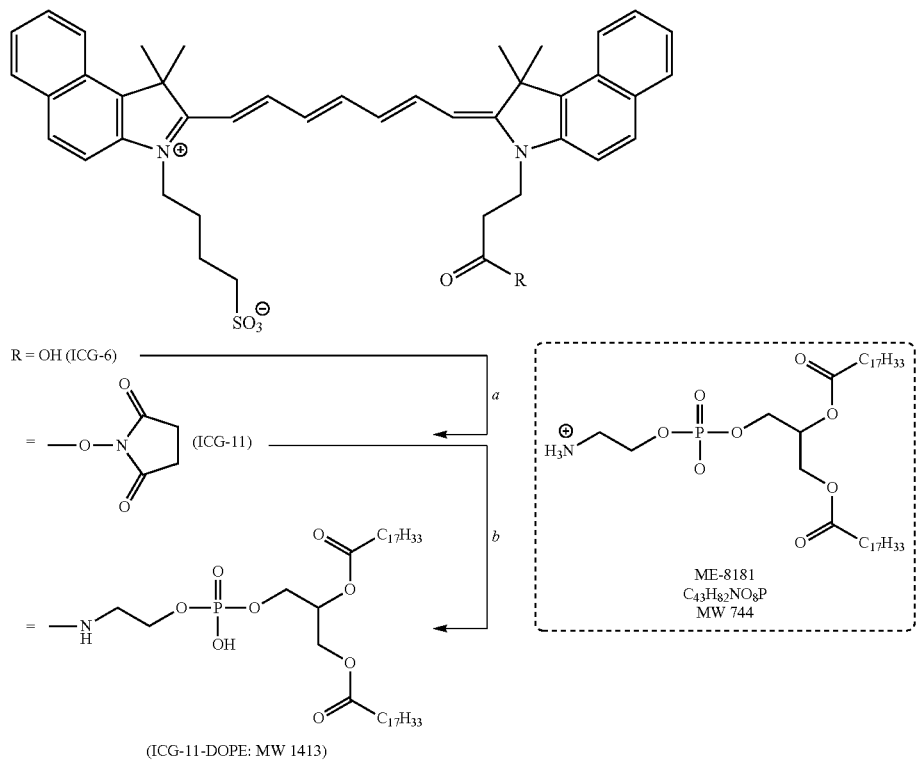

[C47]

(ICG-11-DOPE: MW 1413)

Conditions; $^a$NHS, DCC, MeCN, CHCl$_3$, r.t., 30 min. $^b$ME-8181, Et$_3$N, CHCl$_3$, r.t., 2.5 h, 36% (2 steps).

A fluorescent dye of the present invention that contains another phospholipid moiety can be prepared from ICG-11-DOPE by hydrolyzing a fatty acid phosphate in the presence of a base or acid catalyst or with lipase, and converting the fatty acid moiety by dehydration reaction using a carbodiimide or by an actylation reaction. Alternatively, the fatty acid moiety may be reacted with acyltransferase. These conversion reactions can be easily carried out using methods commonly known in the art, and examples may include those schemes disclosed in Organic Chemistry, Maitland Jones Jr., Tokyo Kagaku Dojin, 2000, and Biochemistry, Lubert Stryer, Tokyo Kagaku Dojin, 2004.

As is demonstrated in the following examples, the fluorescent dyes used in the near-infrared fluorescent imaging TABLE 1-continued

| Name | λ max (EtOH) | Molar Extinction Coefficient (ε) |
|---|---|---|
| ICG-8-C10 | 788 nm | $2.50 \times 10^5$ |
| ICG-11-DOPE | 790 nm | $1.61 \times 10^5$ |

*Manufactured by Tokyo Chemical Industry Co., Ltd. (purity: 80% or more)

Preparation of Fluorescent Probe

The near-infrared fluorescent dye used in the present invention has high affinity for lipids, and is able to stably generate intense fluorescence when conjugated with a liposome. In this description, a conjugate of a near-infrared fluorescent dye and a liposome is referred to as a "fluorescent probe". FIG. 1 shows a schematic diagram of a fluorescent probe of the present invention.

The fluorescent probe of the present invention can be prepared by forming a liposome having a near-infrared fluorescent dye using any method known in the art. For example, the fluorescent probe of the present invention can be prepared by dissolving an indocyanine-based near-infrared fluorescent dye and phospholipid in a suitable organic solvent, drying, dispersing in an aqueous solution, and repeatedly passing through a filter. Alternatively, the fluorescent probe of the present invention may be prepared by ultrasound treatment or reverse phase evaporation as is known in the related art.

Examples of phospholipids for preparing the probe may include phosphatidylcholine, phosphatidylethanolamine, phosphatidylinositol, phosphatidylserine, phosphatidylglycerol, sphingomyelin and phosphatidic acid. Moreover, a lipid component such as cholesterol is preferably added to stabilize the lipid membrane.

The outer surface of the liposome can be modified with a hydrophilic polymer to improve the stability of the liposome in vivo. Examples of such hydrophilic polymers include polyethylene glycol, polymethylethylene glycol, polyhydroxypropylene glycol, polypropylene glycol, polymethylpropylene glycol and polyhydroxypropylene oxide. Polyethylene glycol is particularly preferable.

An example of preparation process of the fluorescent probe of the present invention comprises first dissolving an indocyanine-based near-infrared fluorescent dye, a phospholipid (such as egg yolk lecithin containing phosphatidylcholine), and a lipid (such as cholesterol) or a phospholipid derivative of a hydrophilic polymer (such as a polyethyleneglycol-modified phospholipid) in a suitable organic solvent. The mixing ratio of the near-infrared fluorescent dye to the phospholipid is about 1/1000 to 5/100. Next, the solution is dispersed in an aqueous solution. Alternatively, the organic solvent is removed from the mixture to form a thin film, and an aqueous solution is added. Any physiologically acceptable buffer may be used as an aqueous solution. Preferably, a buffer containing albumin may be used for the purpose of pretreatment that allows the fluorescent probe to form a stable structure in vivo.

Next, liposomes can be formed by passing a suspension containing a phospholipid is dispersed in a buffer through a filter with a pore size of 0.1 μm to 0.2 μm about 10 times to about 30 times. The particle diameter of the liposome can be suitably adjusted by selecting the phospholipid employed, the type and concentration of the lipid and/or modified phospholipid, the pore size of the filter, materials of the filter or the number of times the suspension is passed through the filter. A liposome having a desired diameter can be prepared by sizing the liposome thus formed as necessary. The particle diameter of the liposome is preferably 100 nm to 300 nm and more preferably 150 nm to 250 nm in order to ensure a long anchoring time in lymph nodes. The optimum particle diameter suitable for the target lymph node varies dependent on the tissue being imaged and the type of lymph node, but can be easily selected by those ordinary skill in the art by conducting simple preliminary experiments.

Identification of Sentinel Lymph Node Using Fluorescent Probe for Lymph Node Imaging In order to identify a sentinel lymph node using the fluorescent probe of the present invention, about 200 μL to about 500 μL of the fluorescent probe are directly injected into the submucosal layer, muscle layer or subserous layer around the primary lesion of a tumor. The dispersion medium for dispersion of the fluorescent probe is water. A salt is added to stabilize the fluorescent probe that has the buffering action from pH 6.5 to pH 8.0 at a concentration of 10 mM to 200 mM, such as a phosphate or carbonate, or a sodium salt or potassium salt at a concentration of 10 mM to 500 mM. Serum containing albumin is also effective as a stabilizer. In the case of injecting the dispersion using an endoscope, the fluorescent probe is preferably injected directly using a centesis needle or injection needle for endoscopic treatment. Immediately after direct injection of the fluorescent probe, lymph nodes are observed using a monitoring device and a bioscope such as an endoscope or laparoscope equipped with a filter that only transmits near-infrared light. In this way, lymph nodes where the fluorescent probe of the present invention has accumulated are detected and identified.

Since the fluorescent probe of the present invention has a long anchoring time in sentinel lymph nodes, the sentinel lymph node can be identified with high precision, thereby making is extremely useful for sentinel lymph node navigation surgery.

As used herein, embodiments represented by the expression "comprising" include embodiments represented by the expression "essentially consisting of" as well as aspects represented by the expression "consisting of".

The contents of all patent and reference documents explicitly cited in the description are incorporated herein by reference.

The following provides a more detailed explanation of the present invention through examples thereof, but the present invention is not limited to these examples.

EXAMPLES

Example 1—Synthesis of Fluorescent Dyes ICG-6 and ICG-8

Fluorescent dyes ICG-6 and ICG-8 of the present invention were synthesized according to the scheme indicated below.

[C48]

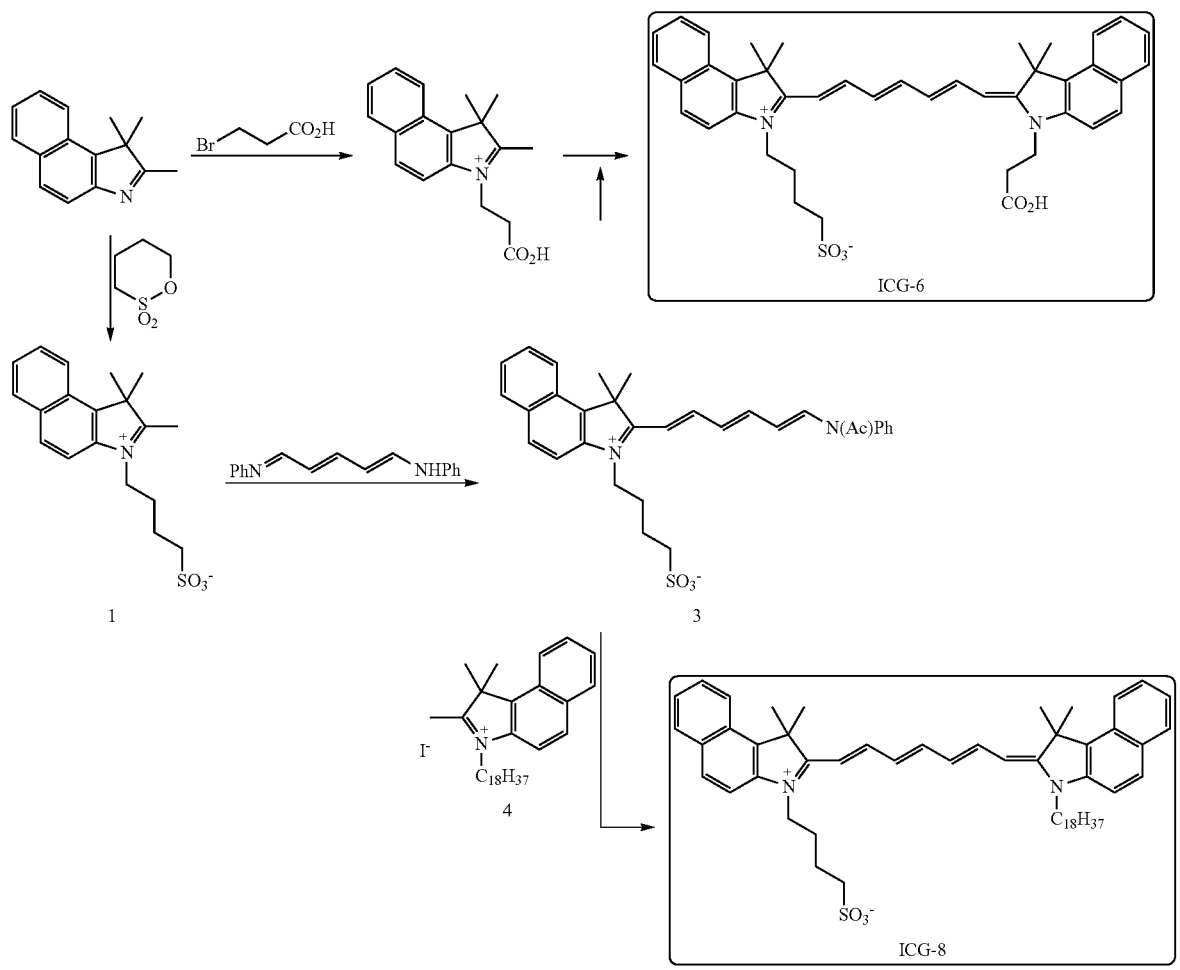

2,3,3-trimethyl-1-(sulfobutyl)-4,5-benzoindolium inner salt (1)

2,3,3-trimethyl-4,5-benzo-3H-indole (3.1 g, 15 mmol) and 1,4-butanesultone (2.1 g, 15 mmol) were mixed in a 25 ml four-mouth flask and filled with nitrogen. After stirring for 4 hours at 80° C., the mixture was allowed to stand to cool to room temperature. Acetone was added and stirred briefly, then the resulting crystals were filtered, washed with 10 ml of acetone, and dried to obtain gray crystals (1.17 g, 23%).

2,3,3-trimethyl-1-(2-carboxyethyl)-4,5-benzoindolium bromide (2)

A mixture of 2,3,3-trimethyl-4,5-benzo-3H-indole (2.3 g, 11 mmol), 3-bromo-1-propionic acid (1.5 g, 9.8 mmol) and acetonitrile (10 ml) was stirred for 16 hours at 65° C., allowed to stand to cool to room temperature, and poured into ethyl acetate (50 ml). The crystals were filtered, washed with acetone, and filtered again, and dried to obtain the titled compound as gray crystals (1.68 g, 47%).

2-(6-acetoanilido-1,3,5-hexatrienyl)-3,3-dimethyl-1-(sulfobutyl)-4,5-benzo[e]indolium inner salt (3)

The indolium salt (1) (1.04 g, 3.0 mmol) and glutaconaldehyde dianil hydrochloride (0.94 g, 3.3 mmol) were mixed in a 25 ml four-mouth flask and stirred for 1 hour at 120° C. The mixture was allowed to stand to cool to room temperature and stirred for 1 hour. The resulting crystals were filtered, washed with acetone, filtered and dried to obtain the titled compound as dark violet crystals (0.91 g, 58%).

4-(2-((1E,3E,5E,7E)-7-(3-(2-carboxyethyl)-1,1-dimethyl-1H-benzo[e]indol-2-(3H)-ylidene) hepta-1,3,5-trienyl)-1,1-dimethyl-1H-benzo[e]indolium-3-yl) butane-1-sulfonic acid (ICG-6)

Compound (2) (0.55 g, 1.5 mmol), Compound (3) (0.80 g, 1.5 mmol) and pyridine (8 ml) were mixed in a 25 ml four-mouth flask, stirred for 45 minutes at 50° C. and allowed to stand to cool to room temperature. The reaction liquid was then concentrated under reduced pressure and water (20 ml) was added to the residue and stirred. 10% hydrochloric acid was added slowly and stirred briefly (pH 3 to pH 4). The resulting crystals were filtered and dried to obtain a crude product (1.12 g). 20 ml of a mixture of methanol and chloroform (5/1) were added to the resulting crystals, stirred with heating, and allowed to stand to cool. The crystals were filtered and recrystallized from a mixture of methanol and chloroform, filtered and allowed to air-dry to obtain ICG-6 as deep green crystals (0.38 g, 37%).

The primary molecular ion peak as determined by LC-MS was m/z=687 (negative). The maximum absorbance wavelength and molar extinction coefficient in ethanol were $\lambda$max=786 nm and $\varepsilon$=1.86×10$^5$, respectively.

1-octadecyl-2,3,3-trimethyl-4,5-benzo[e]indolium iodide (4)

2,3,3-trimethyl-4,5-benzo-3H-indole (8.4 g, 40 mmol), 1-iodooctadecane (16.8 g, 44 mmol) and 2-butanone (30 ml) were mixed in a 100 ml four-mouth flask, stirred for 18 hours at 70° C., allowed to stand to cool to room temperature and ethyl acetate (40 ml) was added. The resulting crystals were filtered, washed (twice) with ethyl acetate, filtered again, and air-dried to obtain the titled compound as gray crystals (4.4 g, 19%).

4(2-((1E,3E,5E,7E)-7-(1,1-dimethyl-3-octadecyl-1H-benzo[e]indol-2 (3H)-ylidene) hepta-1,3,5-trienyl)-1,1-dimethyl-1H-benzo[e]indolium-3-yl) butane-1-sulfonic acid (ICG-8)

Compound (3) (1.58 g, 3.0 mmol), the indolium salt (4) (1.77 g, 3.0 mmol) and pyridine (16 ml) were mixed and dissolved in a 50 ml three-mouth flask, filled with nitrogen and allowed to react for 1 hour at 50° C. The reaction liquid was poured into water (40 ml) and the precipitated crystals were filtered. The resulting crude crystals were dissolved in ethyl acetate, filtered and recrystallized from 40 ml of a mixture of chloroform and ethyl acetate (1/1) to obtain the titled compound as dark green crystals (1.39 g, 53%).

The primary molecular ion peak as determined by LC-MS was m/z=867 (negative). The maximum absorption wavelength and molar extinction coefficient in ethanol were $\lambda$max=787 nm and $\varepsilon$=2.30×10$^5$, respectively.

Example 2—Synthesis of Fluorescent Dye ICG-9

Fluorescent dye ICG-9 of the present invention was synthesized according to the scheme indicated below.

[C49]

p-(di-n-hexylamino)phenol (4)

A mixture of p-aminophenol (0.55 g, 5.0 mmol), 1-iodohexane (2.5 g, 11.8 mmol), potassium carbonate (0.70 g, 5.1 mmol) and dimethylformamide (10 ml) in a 25 ml four-mouth flask was stirred for 3 hours at 75° C. Potassium carbonate (0.70 g, 5.1 mmol) was added and stirred for 6 hours. The mixture was allowed to stand to cool to room temperature, poured into water and extracted with ethyl acetate. The organic layer was washed with water (3 times) and saturated salt solution, dried over anhydrous sodium sulfate and concentrated under reduced pressure to obtain a crude product (1.3 g). The crude product was purified by silica gel column chromatography (toluene/ethyl acetate=25/1 to 15/1) to obtain the titled compound as an oil (0.81 g, 58%).

3-chloro-2,4-trimethylene glutaconaldehyde dianil hydrochloride (5)

Dimethylformamide (55 ml) was placed in a 300 ml four-mouth flask and phosphorous oxychloride (50 ml, 0.54 mol) was added dropwise for 1 hour at 10° C. or lower. The mixture was slowly heated and cyclohexanone (15 g, 0.15 mol) and dimethylformamide (35 ml) were added dropwise for 1 hour at 45° C. to 50° C. After stirring for 3 hours at 50° C., the reaction liquid was allowed to stand to cool to room temperature, poured into water and stirred overnight. The crystals were filtered, washed with water, and filtered again, and dried overnight to obtain the aldehyde as yellow crystals (19.4 g, 74%). The aldehyde (19 g, 0.1 mol) and dimethylformamide (75 ml) were mixed in a 500 ml four-mouth flask, and concentrated hydrochloric acid (25 ml) was added dropwise at 8° C. or lower. After stirring for 15 minutes, a mixture of aniline (21.5 g, 0.23 mol) and ethanol (110 ml)

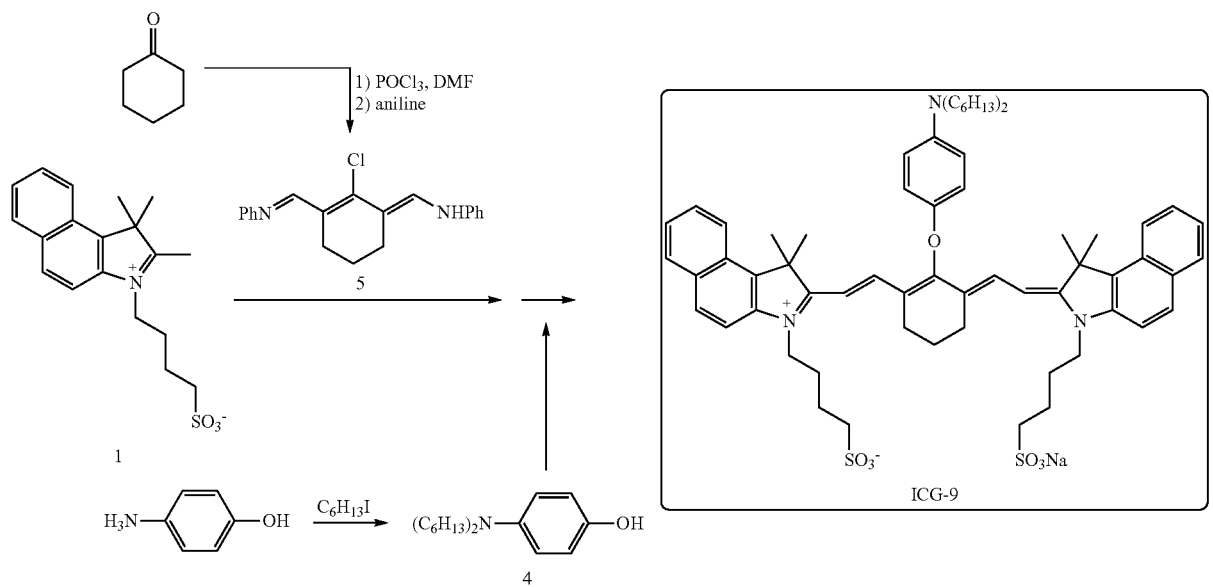

A was added dropwise at 7° C. or lower. The mixture was allowed to warm to room temperature for 1.5 hours, poured into water, and stirred for 1 hour. The resulting crystals were filtered and air-dried to obtain the titled compound (41.3 g, quantitative).

Sodium 4-(2-((E)-2-((E)-2-(4-(dihexyamino) phenoxy)-3-((E)-2-(1,1-dimethyl-3-(4-sulfonatebutyl)-1H-benzo[e]indol-2 (3H)-ylidene)ethylidene)cyclohexenyl)vinyl)-1,1-dimethyl-1H-benzo[e]indolium-3-yl)butane-1-sulfonate (ICG-9)

Compound (1) (0.83 g, 2.4 mmol), 3-chloro-2,4-trimethylene glutaconaldehyde dianil hydrochloride (0.43 g, 1.2 mmol), triethylamine (1.1 ml, 7.9 mmol) and methanol (12 ml) were mixed in a 25 ml four-mouth flask and filled with nitrogen. Acetic anhydride was then added dropwise to the reaction liquid for 5 minutes, and stirred for 15 hours while protecting from light. Sodium acetate (0.49 g, 6.0 mmol) was added to the reaction liquid and evaporated the solvent under reduced pressure. The residue was then dissolved in acetone to remove insoluble materials, and the filtrate was concentrated under reduced pressure. The residue was washed with ethyl acetate and subsequently with acetone, filtered, and air-dried to obtain crude crystals of the cyanine dye (0.87 g).

Sodium hydride (60%, 0.05 g, 1.3 mmol) and dimethylformamide (2 ml) were mixed in a 25 ml four-mouth flask and the phenol derivative (4) (0.30 g, 1.1 mmol) and dimethylformamide (3 ml) were added dropwise for 10 minutes in a nitrogen atmosphere at 65° C. or lower. After gradually warming to room temperature, the mixture was stirred for 1 hour to prepare a sodium phenoxide. Then the previously synthesized cyanine dye (0.80 g, 0.94 mmol) and dimethylformamide (9 ml) were mixed in a 50 ml four-mouth flask, phenoxide dimethylformamide solution was added dropwise for 10 minutes in a nitrogen atmosphere. After stirring for 3 hours, dry ice (1 g) was added and the reaction liquid was purified by silica gel column chromatography (chloroform/methanol=30/1 to 3/2). The resulting crude crystals were washed with a mixture of ethyl acetate and a small amount of acetone, filtered and air-dried to obtain ICG-9 as deep green crystals (0.49 g, 48%).

The primary molecular ion peak as determined by LC-MS was m/z=1069 (negative). The maximum absorbance wavelength and molar extinction coefficient in ethanol were λmax=810 nm and ε=1.24×10$^5$, respectively.

Example 2-2

Synthesis of Additional Compounds

ICG-8-C4

4(2-((1E,3E,5E,7E)-7-(1,1-dimethyl-3-butyl-1H-benzo[e]indol-2(3H)-ylidene) hepta-1,3,5-trienyl)-1,1-dimethyl-1H-benzo[e]indolium-3-yl) butane-1-sulfonic acid (ICG-8-C4)

1-butyl-2,3,3-trimethyl-4,5-benzo[e]indolium iodide (10.7 g, 62%) was obtained in the same manner as Example 1 with replacing 1-iodooctadecane (16.8 g, 44 mmol) (used for the synthesis of 1-octadecyl-2,3,3-trimethyl-4,5-benzo[e]indolium iodide (4) in Example 1) with 1-iodobutane (12.1 g, 66 mmol). The titled compound (1.35 g, 44%) was obtained in the same manner as the synthesis of ICG-8. The primary molecular ion peak as determined by LC-MS was m/z=673 (positive). The maximum absorbance wavelength and molar extinction coefficient in ethanol were λmax=787 nm and ε=2.52×10$^5$, respectively.

ICG-8-C6

4(2-((1E,3E,5E,7E)-7-(1,1-dimethyl-3-hexyl-1H-benzo[e]indol-2 (3H)-ylidene) hepta-1,3,5-trienyl)-1,1-dimethyl-1H-benzo[e]indolium-3-yl) butane-1-sulfonic acid (ICG-8-C6)

1-hexyl-2,3,3-trimethyl-4,5-benzo[e]indolium iodide (5.63 g, 54%) was obtained in the same manner as Example 1 with replacing 1-iodooctadecane (16.8 g, 44 mmol) (used for the synthesis of 1-octadecyl-2,3,3-trimethyl-4,5-benzo[e]indolium iodide (4) in Example 1) with 1-iodohexane (6.4 g, 30 mmol). The titled compound (1.18 g, 57%) was obtained in the same manner as the synthesis of ICG-8. The primary molecular ion peak as determined by LC-MS was m/z=701 (positive). The maximum absorbance wavelength and molar extinction coefficient in ethanol were λmax=787 nm and ε=2.34×10$^5$, respectively.

ICG-8-C8

4(2-((1E,3E,5E,7E)-7-(1,1-dimethyl-3-octyl-1H-benzo[e]indol-2 (3H)-ylidene) hepta-1,3,5-trienyl)-1,1-dimethyl-1H-benzo[e]indolium-3-yl) butane-1-sulfonic acid (ICG-8-C8)

1-octyl-2,3,3-trimethyl-4,5-benzo[e]indolium iodide (11.7 g, 59%) was obtained in the same manner as Example 1 with replacing 1-iodooctadecane (16.8 g, 44 mmol) (used for the synthesis of 1-octadecyl-2,3,3-trimethyl-4,5-benzo[e]indolium iodide (4) in Example 1) with 1-iodooctane (15.8 g, 66 mmol). The titled compound (0.93 g, 59%) was obtained in the same manner as the synthesis of ICG-8. The primary molecular ion peak as determined by LC-MS was m/z=727 (positive). In addition, the maximum absorbance wavelength and molar extinction coefficient in ethanol were λmax=788 nm and ε=2.63×10$^5$, respectively.

ICG-8-C10

4(2-((1E,3E,5E,7E)-7-(1,1-dimethyl-3-decyl-1H-benzo[e]indol-2(3H)-ylidene)hepta-1,3,5-trienyl)-1,1-dimethyl-1H-benzo[e]indolium-3-yl)butane-1-sulfonic acid (ICG-8-C10)

1-decyl-2,3,3-trimethyl-4,5-benzo[e]indolium iodide (4.83 g, 23%) was obtained in the same manner as Example 1 with replacing 1-iodooctadecane (16.8 g, 44 mmol) (used for the synthesis of 1-octadecyl-2,3,3-trimethyl-4,5-benzo[e]indolium iodide (4) in Example 1) with 1-iododecane (17.7 g, 66 mmol). The titled compound (0.79 g, 46%) was obtained in the same manner as the synthesis of ICG-8.

ICG-11-DOPE:

Coatsome ME-8181 (manufactured by NOF Corp.) was used as a phospholipid to be modified.

[C50]

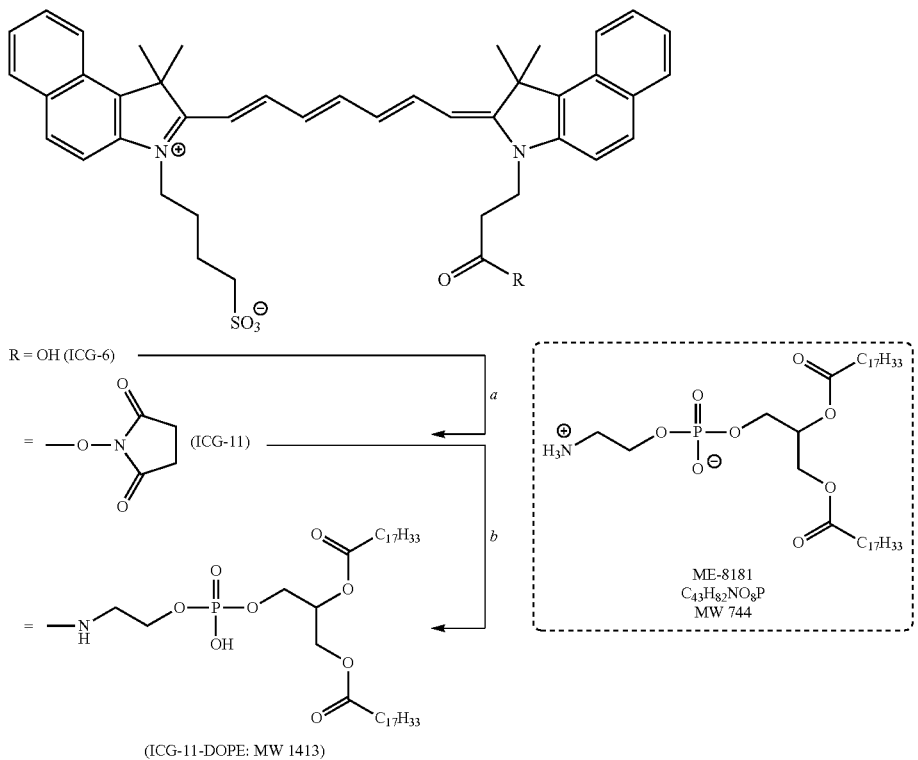

(ICG-11-DOPE: MW 1413)

Conditions; <sup>a</sup>NHS, DCC, MeCN, CHCl₃, r.t., 30 min. <sup>b</sup>ME-8181, Et₃N, CHCl₃, r.t., 2.5 h, 36% (2 steps).

ICG-6 (0.5 g, 0.73 mmol), N-hydroxysuccinimide (0.17 g, 1.5 mmol), acetonitrile (3 mL) and chloroform (10 mL) were placed in a 25 mL four-mouth flask and filled with nitrogen. A mixture of dicyclohexylcarbodiimide (0.30 g, 1.5 mmol) and chloroform (2 mL) was added dropwise for 10 minutes at 2° C. The reaction liquid was slowly warmed to room temperature, stirred for 30 minutes and filtered. The filtrate was concentrated under reduced pressure at 25° C. or lower, and the residue was triturated with ethyl acetate. The crystals were collected by filtration and washed with acetone to obtain crude crystals of ICG-11 (0.66 g). Then the resulting crystals (0.66 g, ca. 0.73 g) and chloroform (10 mL) were placed in a 25 mL four-mouth flask and a mixture of Coatsome ME-8181 (0.54 g, 0.73 mmol), triethylamine (0.10 g, 1.0 mmol) and chloroform (5 mL) was added dropwise for 20 minutes in a nitrogen atmosphere. The reaction liquid was stirred for 2.5 hours at room temperature, filtered and concentrated. The residue was purified with a flash column ($SiO_2$, $CHCl_3$/MeOH=4/1 to 3/1) to obtain ICG-11-DOPE (0.37 g, 36%).

Example 3—Preparation of Fluorescent Probe

Egg yolk phosphatidylcholine (7.3 mg), cholesterol (0.4 mg), phosphatidylethanolamine-N-methoxypolyethylene glycol 5000-dioleoyl-glyceroammonium salt (3.2 mg) and a fluorescent dye (ICG, ICG-6, ICG-8 or ICG-9) (3.2 mM to $3.2 \times 10^{-4}$ mM) were dissolved in a mixture of chloroform and methanol (volume percentage: 9:1). The organic solvent was evaporated under reduced pressure to form a thin film. 1 mL of an aqueous solution of 5% human albumin (CSL Behring GmbH) was then added and allowed to stand for several hours at room temperature. The suspension was then passed through a polycarbonate filter (pore size: 0.1 μm to 0.2 μm, Millipore Corp.) attached to a membrane holder (Millipore Corp.) about 10 times to form liposomes.

Fluorescence properties of the ICG-8-containing fluorescent probe obtained in this manner were then examined. The fluorescence spectrum was measured by exciting at 738 nm. The excitation spectrum was measured by detecting fluorescence at 850 nm when excited at each wavelength from 600 nm to 800 nm. The results are shown in FIG. 2. FIGS. 3A and 3B indicate the fluorescence spectra of a dispersion of each fluorescent probe at an excitation wavelength of 738 nm (ICG derivative concentration: $3.2 \times 10^2$ mM).

The particle diameter distribution of the resulting liposomes was measured using a dynamic light scattering particle size distribution analyzer (Nikkiso Co., Ltd.). The results are shown in FIG. 4.

Example 4-1—Fluorescence Detectability of Fluorescent Probe In Vitro

Near-infrared fluorescence intensity was measured for the fluorescent dye-containing liposomes prepared in the manner described above with an aqueous solution of ICG serving as a control. 100 μL of liposome suspension containing a dye of a predetermined concentration or the ICG aqueous solution were added to a 96-well plate and irradiated with excitation light (LED light source, <780 nm) to detect the generated fluorescence (>810 nm). Brightness was evaluated using Image J image processing software.

The results are shown in Table 2. In the table, values indicate the brightness score as determined with the Image J software (maximum value: 255), with the values shown in parentheses indicate the standard deviation.

TABLE 2

| Concentration (mM) | ICG fluorescent probe | ICG-6 fluorescent probe | ICG-8 fluorescent probe | ICG-9 fluorescent probe | ICG aqueous solution (control) |
|---|---|---|---|---|---|
| $3.2 \times 10^0$ | 55(5) | 72(6) | 36(5) | 31(6) | 27(5) |
| $3.2 \times 10^{-1}$ | 56(5) | 81(5) | 84(6) | 52(4) | 38(6) |
| $3.2 \times 10^{-2}$ | 173(7) | 195(6) | 217(6) | 143(5) | 98(5) |
| $3.2 \times 10^{-3}$ | 158(4) | 181(5) | 189(4) | 149(4) | 118(10) |
| $3.2 \times 10^{-4}$ | 84(4) | 95(4) | 105(5) | 77(6) | 61(7) |

| Concentration (mM) | ICG-8-C4 fluorescent probe | ICG-8-C6 fluorescent probe | ICG-8-C8 fluorescent probe | ICG-8-C10 fluorescent probe | ICG-8-C18 fluorescent probe | ICG-11-DOPE fluorescent probe |
|---|---|---|---|---|---|---|
| $3.2 \times 10^{-1}$ | 47(5) | 66(7) | 49(8) | 39(7) | 51(8) | — |
| $3.2 \times 10^{-2}$ | 155(10) | 161(13) | 163(9) | 156(11) | 164(9) | 187(12) |
| $3.2 \times 10^{-3}$ | 141(8) | 137(6) | 138(6) | 153(10) | 138(6) | — |
| $3.2 \times 10^{-4}$ | 68(6) | 68(7) | 67(8) | 77(9) | 58(6) | — |

The fluorescent probes obtained by incorporating a near-infrared fluorescent dye in the liposomes according to the present invention demonstrated extremely high fluorescence intensity as compared to the ICG aqueous solution.

Example 4-2—Fluorescence Lifetime of Fluorescence Probes

The fluorescence lifetimes of the fluorescence probes of the present invention were measured. The TemPro fluorescence lifetime photometer (manufactured by Horiba, Ltd.) was used for measurement. Table 3 indicates the values for a chloroform solution containing each near-infrared fluorescent dye at a concentration of $3.2 \times 10^{-2}$ mM and an aqueous solution of ICG (control), and Table 4 indicates values obtained from each of the near-infrared fluorescent dyes incorporated in the liposomes at a concentration of $3.2 \times 10^{-2}$ mM. A 740 nm semiconductor laser was used for the excitation light, and the lifetime spectra obtained at a fluorescence wavelength of 816 nm was analyzed for two components. The results are shown in Table 3 and Table 4.

TABLE 3

| Name | ICG-8-C6 | ICG-8-C10 | ICG-8-C18 | ICG aqueous solution (control) |
|---|---|---|---|---|
| First component (ns) | 1.25 | 1.27 | 1.26 | 0.01~0.15 |
| First component (%) | 69 | 67 | 68 | |
| Second component (ns) | 0.31 | 0.41 | 0.37 | |
| Second component (%) | 31 | 33 | 32 | |

TABLE 4

| Name | ICG-8-C6 fluorescent probe | ICG-8-C10 fluorescent probe | ICG-8-C18 fluorescent probe |
|---|---|---|---|
| First component (ns) | 0.41 | 0.39 | 0.38 |
| First component (%) | 90 | 93 | 82 |
| Second component (ns) | 0.77 | 0.83 | 0.65 |
| Second component (%) | 10 | 7 | 18 |

All of the fluorescent probe dispersions showed the fluorescence lifetime longer than the ICG aqueous solution, and demonstrating superior sensitivity of near-infrared fluorescent imaging. Moreover, differences in the alkyl chains of the substituents have little effect on fluorescence lifetime of the fluorophore. These results indicate that the design of the skeletal structure of the near-infrared fluorescent dye of the invention is useful for preparing fluorescent probes.

Example 5—Fluorescence Detectability of Fluorescent Probes In Vivo

In order to investigate the fluorescence detectability of the fluorescent probes in vivo, an ICG-8-containing fluorescent probe dispersion (0.2 mL, 10 mM as phospholipid concentration) was injected into the foreleg of mice (indicated with a yellow arrow in FIG. 5). The dispersion medium of the fluorescent probe dispersion was an aqueous solution of 5% human albumin (CSL Behring GmbH). The concentration of phospholipid in the dispersion was determined from the total weight of lipid used and the volume of the dispersion medium added to the dispersion, and was indicated as a phospholipid concentration that shows the amount per unit volume of the liposome-type fluorescent probe. Ten minutes later, the epidermal tissue was peeled off, and the site was irradiated with excitation light (LED light source, <780 nm) and the generated fluorescence (>810 nm) was detected with a monochromatic camera. A visible light image is shown in FIG. 5A, while a fluorescent image is shown in FIG. 5B. As is clear from FIG. 5B, fluorescence was emitted at the injection site of the fluorescent probe dispersion, and the fluorescent probe anchored to the popliteal lymph node was detected (circled)

Example 6—Fluorescent Probe Anchoring Property in Mouse Popliteal Lymph Node

In order to investigate e lymph node anchoring property of the fluorescent probe, an ICG-8-containing fluorescent probe dispersion (liposome mean particle diameter: 240 nm, 0.2 mL, phospholipid concentration: 10 mM) or an ICG aqueous solution serving as a control (0.2 mL, 3.2 mM) was injected into the foreleg of mice (FIG. 6A) in the same manner as Example 5. Ter minutes later, the epidermal tissue was peeled off, and the site was irradiated with excitation light (LED light source, <780 nm) and the generated fluorescence (>810 nm) was detected with a monochromatic camera.

When the ICG aqueous solution was injected, fluorescent was emitted at the first popliteal lymph node from the foreleg as well as from the second external iliac lymph node from the foreleg (solid white circles in FIGS. 6B and 6C). On the other hand, when the ICG-8-containing fluorescent probe dispersion was injected, fluorescent was detected from the popliteal lymph node, but not detected at the external iliac lymph node (dotted line white circles in FIGS. 6B and 6C). FIG. 6C is an image of fluorescence detected from the back side at the same location as FIG. 6B. These findings indicate that the ICG-8-containing fluorescent probe have a longer anchoring time in the popliteal lymph node in comparison with the ICG aqueous solution. In the case of using an ICG-8-containing fluorescent probe dispersion having a liposome mean particle diameter of 120 nm, fluorescence was detected in both the popliteal lymph node and external iliac lymph node, and anchoring time in the popliteal lymph node was longer than with a liposome mean particle diameter of 240 nm.

To investigate primary lymph node anchoring rate after the passage of a prescribed amount of time, an ICG-8-containing fluorescent probe or ICG aqueous solution was administered to mice in the same manner as described above. The results are indicated as (number of mice in which fluorescence was observed in primary lymph node only/total number of mice in the experiment). The p-values were calculated using Fisher's exact test.

TABLE 5

| Elapsed time from administration (h) | No. of mice in which fluorescence was observed in primary lymph node only/total no. of mice in experiment | | P value |
|---|---|---|---|
| | ICG-8-containing fluorescent probe | ICG aqueous solution | |
| 1 | 13/13 | 0/4 | 0.01 |
| 3 | 15/19 | 2/5 | 0.13 |
| 6 | 6/12 | 0/4 | 0.12 |
| 24 | 1/4 | 0/3 | 0.57 |

These results indicate that the ICG-8-containing fluorescent probe demonstrates a significantly higher anchoring rate to the primary lymph node than ICG at 1 hour after administration. The ICG-8-containing fluorescent probe tended to demonstrate a higher anchoring rate than ICG at 3 hours or 6 hours after administration as well.

Example 7—Anchoring Property of Fluorescent Probe in Porcine Sigmoid Lymph Node 0.2 mL of ICG-8-containing fluorescent probe (liposome mean particle diameter: 240 nm) were injected into the digestive tract of a pig at the sigmoid colon (indicated with a yellow arrow in FIG. 7). After 30 minutes, fluorescence was detected with excitation light (<800 nm) and detection light (>810 nm) using an internal varistor-type endoscope and a fluorescence observation-type laparoscope. Fluorescence was detected from a mesenteric primary lymph node that is visually distinguished (dotted line white circle in FIG. 7B), and also from an buried mesenteric primary lymph node that is not visually distinguished (solid white circle in FIG. 7B). Namely, when the ICG-8-containing fluorescent probe dispersion was injected, fluorescence was emitted only from the (two) primary lymph nodes that were closest to the injection site among the multiple mesenteric lymph nodes, while fluorescence was not observed from other lymph nodes. These findings suggested that the ICG-8-containing fluorescent probe dispersion is useful for detecting fluorescence of sentinel lymph nodes.

Example 8—Anchoring Property of Fluorescent Probe in Porcine Subpyloric Lymph Node 0.2 mL of ICG-8-containing fluorescent probe (liposome mean particle diameter: 160 nm) dispersed in physiological saline were injected into the stomach wall in the pyloric region of a pig (FIG. 8A). Thirteen minutes later, fluorescence was detected with excitation light (<800 nm) and detection light (>810 nm) using an internal varistor-type endoscope and a fluorescence observation-type laparoscope. Fluorescence was visually detected from the primary lymph nodes of the stomach connected to the pyloric region (dotted line white circles in FIG. 8B). Namely, the ICG-8-containing fluorescent probe dispersed in physiological saline, that has a minimal effect on the body, was found to be useful for detecting fluorescence of sentinel lymph nodes.

INDUSTRIAL APPLICABILITY

The near-infrared fluorescent imaging agent of the present invention is useful for detecting sentinel lymph nodes during cancer and other surgeries.

The invention claimed is:

1. A fluorescent probe for near-infrared fluorescent imaging in sentinel lymphadenography comprising a liposome containing a fluorescent dye having a hexatriene skeletal structure, wherein the fluorescent dye having a hexatriene skeletal structure is a compound represented by chemical formula (V):

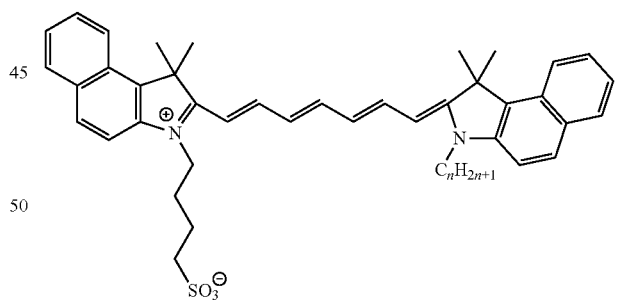

wherein, n represents an integer of 4 to 18.

2. The fluorescent probe for near-infrared fluorescent imaging in sentinel lymphadenography according to claim 1, wherein the particle diameter of the liposome is 100 nm to 300 nm.

3. The fluorescent probe for near-infrared fluorescent imaging in sentinel lymphadenography according to claim 1, wherein the particle diameter of the liposome is 150 nm to 250 nm.

4. A near-infrared fluorescent imaging agent comprising a compound represented by chemical formula (V):

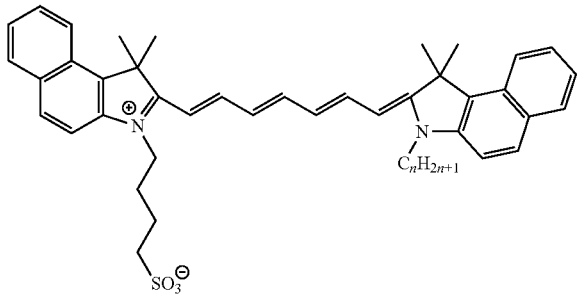

(V)

wherein, n represents an integer of 4 to 18.

5. A method for identifying a sentinel lymph node in a subject, comprising administering to the subject the fluorescent probe according to claim 1 and detecting fluorescence generated from the fluorescent probe.

6. A compound represented by chemical formula (V):

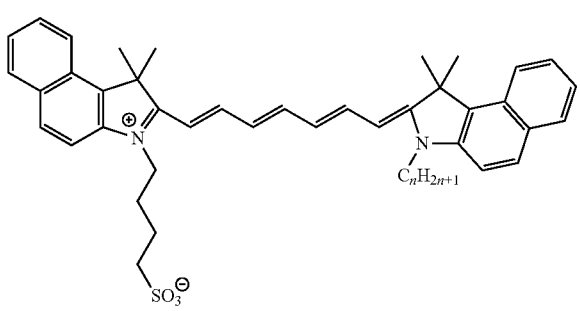

(V)

wherein, n represents an integer of 4 to 18.

7. A liposome comprising the compound according to claim 6.

8. The compound according to claim 6, wherein n is 4.

9. The compound according to claim 6, wherein n is 6.

10. The compound according to claim 6, wherein n is 8.

11. The compound according to claim 6, wherein n is 10.

12. The compound according to claim 6, wherein n is 18.

13. A liposome comprising the compound according to claim 8.

14. A liposome comprising the compound according to claim 9.

15. A liposome comprising the compound according to claim 10.

16. A liposome comprising the compound according to claim 11.

17. A liposome comprising the compound according to claim 12.

18. A method for identifying a sentinel lymph node in a subject, comprising administering to the subject the compound according to claim 8 and detecting fluorescence generated from the compound.

19. A method for identifying a sentinel lymph node in a subject, comprising administering to the subject the compound according to claim 9 and detecting fluorescence generated from the compound.

20. A method for identifying a sentinel lymph node in a subject, comprising administering to the subject the compound according to claim 10 and detecting fluorescence generated from the compound.

21. A method for identifying a sentinel lymph node in a subject, comprising administering to the subject the compound according to claim 11 and detecting fluorescence generated from the compound.

22. A method for identifying a sentinel lymph node in a subject, comprising administering to the subject the compound according to claim 12 and detecting fluorescence generated from the compound.

23. A method for identifying a sentinel lymph node in a subject, comprising administering to the subject the liposome according to claim 13 and detecting fluorescence generated from the liposome.

24. A method for identifying a sentinel lymph node in a subject, comprising administering to the subject the liposome according to claim 14 and detecting fluorescence generated from the liposome.

25. A method for identifying a sentinel lymph node in a subject, comprising administering to the subject the liposome according to claim 15 and detecting fluorescence generated from the liposome.

26. A method for identifying a sentinel lymph node in a subject, comprising administering to the subject the liposome according to claim 16 and detecting fluorescence generated from the liposome.

27. A method for identifying a sentinel lymph node in a subject, comprising administering to the subject the liposome according to claim 17 and detecting fluorescence generated from the liposome.

* * * * *